United States Patent [19]

Skuballa et al.

[11] Patent Number: 5,187,286
[45] Date of Patent: Feb. 16, 1993

[54] LEUKOTRIENE-B4 DERIVATIVES, PROCESS FOR THEIR PRODUCTION AND THEIR USE AS PHARMACEUTICAL AGENTS

[75] Inventors: Werner Skuballa; Bernd Buchmann; Josef Heindl; Wolfgang Frohlich; Roland Ekerdt, all of Berlin, Fed. Rep. of Germany

[73] Assignee: Schering Aktiengesellschaft, Berlin and Bergkamen, Fed. Rep. of Germany

[21] Appl. No.: 663,927

[22] PCT Filed: May 25, 1990

[86] PCT No.: PCT/DE90/00397

§ 371 Date: Mar. 25, 1991

§ 102(e) Date: Mar. 25, 1991

[87] PCT Pub. No.: WO90/14329

PCT Pub. Date: Nov. 29, 1990

[30] Foreign Application Priority Data

May 26, 1989 [DE] Fed. Rep. of Germany ....... 3917597

[51] Int. Cl.$^5$ ..................... C07D 311/02; C07C 67/02
[52] U.S. Cl. .................................. 549/283; 560/126; 560/127; 560/231; 560/254; 562/507; 562/508; 564/79; 564/80; 564/89; 564/152; 564/171; 568/605; 568/611; 568/667; 568/669; 568/670; 568/807; 568/823; 568/825; 568/826
[58] Field of Search ............... 560/126, 127, 231, 254; 562/507, 508; 564/79, 80, 89, 152, 171; 568/608, 611, 667, 669, 670, 807, 823, 825, 826; 574/451, 532, 557; 514/568; 549/283

[56] References Cited

PUBLICATIONS

Morris J. et al. Tetrahedron Letters (29) No. 2 1988 pp. 143–146.
Borgeat et al., Prostaglandins 35 Nr. 5 May 1988 pp. 723–731.

Primary Examiner—Paul J. Killos
Attorney, Agent, or Firm—Millen, White Zelano and Branigan

[57] ABSTRACT

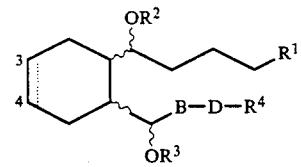

(I)

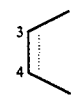

(a)

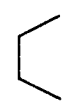

(II)

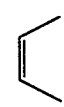

(III)

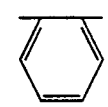

(IV)

Compounds of formula (I) in which the residues have the following meanings: a is (II) or (III); $R^1$ is $CH_2OH$, $CH_3$, $CF_3$, $COOR^5$ with $R^5$ or, A is a trans, trans—CH=CH—CH=CH— or tetramethylene group; B is an alkylene group with up to 10 C atoms; D is a direct bond, oxygen, sulphur, a —C≡C—group or a —CH=CR$^7$—group, or (IV); B and D together are a direct bond; $R^2$ and $R^3$ are the same or different and denote hydrogen or an organic acid residue with 1 to 15 C atoms, $R^1$ and $R^2$ together are a carbonyl group; $R^4$ is a hydrogen atom or $C_{1-10}$ alkyl, and if $R^5$ denotes a hydrogen atom, their salts with physiologically acceptable bases and their cyclodextrin clathrates.

18 Claims, No Drawings

LEUKOTRIENE-B4 DERIVATIVES, PROCESS FOR THEIR PRODUCTION AND THEIR USE AS PHARMACEUTICAL AGENTS

The invention relates to new leukotriene-B4 derivatives, the process for their production as well as their use as pharmaceutical agents.

Leukotriene B4 (LTB4) was discovered in 1979 by B. Samuelsson et al. as a metabolite of arachidonic acid. In the biosynthesis, leukotriene A4 is formed by the enzyme 5-lipoxygenase first as a central intermediate product, which then is converted by a specific hydrolase to the LTB4.

KEY

Arachidonsaeure = arachidonic acid
Lipoxygenase = lipoxygenase
Dehydrase = dehydrase
Leukotrien A4 (LTA4) = leukotriene A4 (LTA4)
Hydrolase = hydrolase
Glutathion – S-transferase = glutathione – S-transferase
Leukotrien B4 (LTB4) = leukotriene B4 (LTB4)
Leukotrien C4 (LTC4) = leukotriene C4 (LTC4)

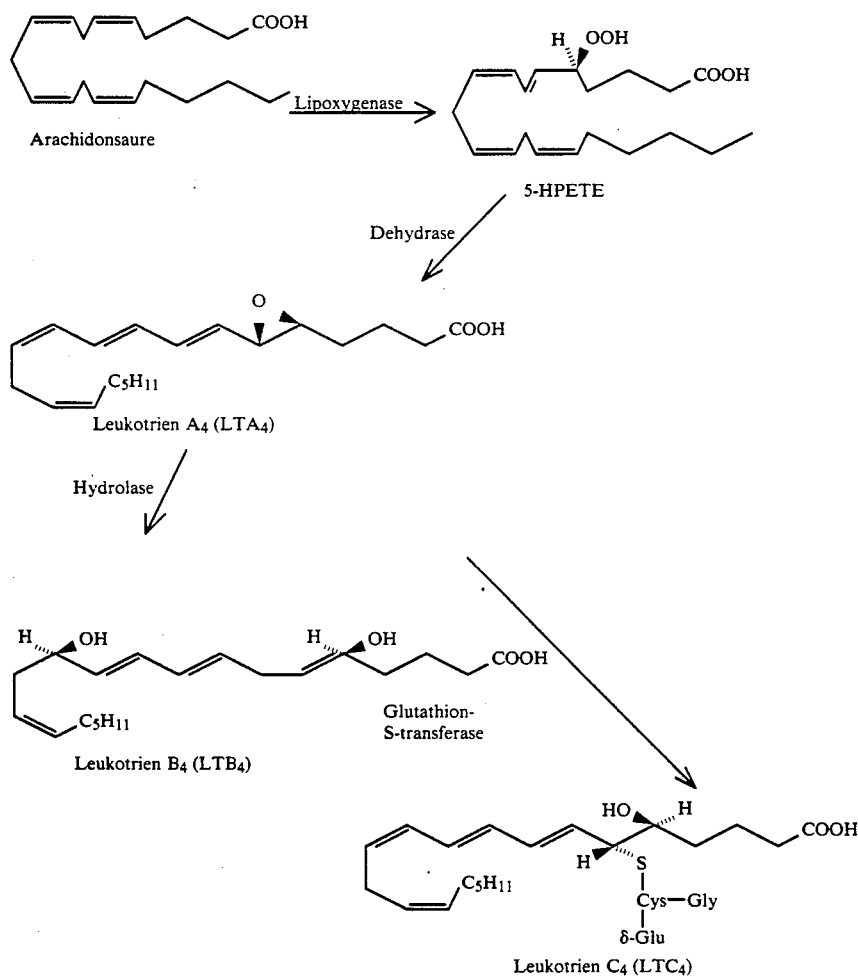

The nomenclature of the leukotrienes can be gathers from the following works:
a) B. Samuelsson et al., Prostaglandins 19, 645 (1980); 17, 785 (1979).
b. C. N. Serhan et al., Prostaglandins 34, 201 (1987).

The physiological and especially the pathophysiological importance of leukotriene B4 is summarized in several more recent works: 1: The Leukotriene, Chemistry and Biology eds. L. W. Chakrin, D. M. Bailey, Academic Press 1984. b) J. W. Gillard et al., Drugs of the Future 12, 453 (1987). c) B. Samuelsson et al., Science 237, 1171 (1987). d) C. W. Parker, Drug Development Research 10, 277 (1987). It follows from the above that LTB4 is an important inflammation mediator for inflammatory diseases, in which leukocytes invade the affected tissue.

It is known that LTB4 causes the adhesion of leukocytes on the blood vessel wall. LTB4 is chemotactically effective, i.e., it triggers a directed migration of leukocytes in the direction of a gradient of increasing concentration. Further, because of its chemotactic activity, it indirectly changes the vascular permeability, and a synergism with prostaglandin E2 is observed. LTB4 obviously plays a decisive role in inflammatory, allergic and immunological processes.

Leukotrienes and especially LTB4 are involved in skin diseases, which accompany inflammatory processes (increased vessel permeability and formation of edemas, cell infiltration), increased proliferation of skin cells and itching, such as, for example, in eczemas, erythemas, psoriasis, pruritus and acne. Pathologically increased leukotriene concentrations are involved either causally in the development of many dermatitides or there is a connection between the persistence of the dermatitides and the leukotrienes. Clearly increased leukotriene concentrations were measured, for example, in the skin of patients with psoriasis or atopic dermatitis.

Further, leukotrienes and $LTB_4$ are involved especially in arthritis, chronic lung diseases (e.g., asthma), rhinitis and inflammatory intestinal diseases.

Antagonists against $LTB_4$ receptors or inhibitors of those enzymes, which are involved in the synthesis of the $LTB_4$, should be effective as specific medications, especially against diseases which accompany inflammations and allergic reactions.

Besides the therapeutic possibilities, which can be derived from an antagonizing of $LTB_4$ with $LTB_4$ analogs, the usefulness and potential use of leukotriene-$B_4$ agonists for the treatment of fungus diseases of the skin was also able to be shown recently (H. Kayama, Prostaglandins 34, 797 (1988)).

It has now been found that the incorporation of the chemically and metabolically labile cis-delta$^{6,7}$ double bond of $LTB_4$ in a cis-1,2-substituted cyclohexyl ring or a trans-1,2-substituted cyclohexyl ring results in a stabilization, and especially by further derivatizing of the functional groups, $LTB_4$ derivatives are obtained which greatly antagonize the action of the natural $LTB_4$. I.e., the invention comprises $LTB_4$ analogs, which can act as antagonists.

The invention relates to compounds of formula I,

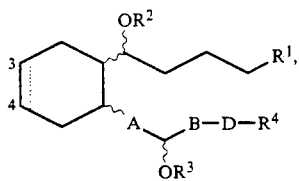

in which the radicals have the following meanings:

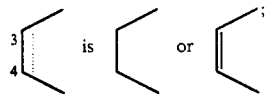

$R^1$ is $CH_2OH$, $CH_3$, $CF_3$, $COOR^5$ with $R^5$ meaning a hydrogen atom, an alkyl radical with 1–10 C atoms, a cycloalkyl radical with 3–10 C atoms, an aryl radical with 6–10 C atoms optionally substituted by 1–3 chlorine, bromine, phenyl, $C_{1-4}$ alkyl, $C_{1-4}$ alkoxy, chloromethyl, fluoromethyl, trifluoromethyl, carboxy or hydroxy, a —$CH_2$—CO—aryl radical with 6–10 C atoms for an aryl or a 5–6-member aromatic heterocyclic radical with at least 1 heteroatom, or $R^1$ is $CONHR^6$ with $R^6$ meaning an alkanoyl radical or an alkanesulfonyl radical with 1–10 C atoms or radical $R^5$;

A is a trans, trans—CH=CH—CH=CH— group or a tetramethylene group;

B is a straight-chain or branched-chain, saturated or unsaturated alkylene group with up to 10 C atoms which can optionally be substituted by fluorine, or the group

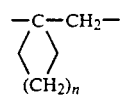

with n=1–3;

D is a direct bond, oxygen, sulfur, a —C≡C group or a —CH=CR$^7$ group with R$^7$ as hydrogen, $C_{1-5}$ alkyl, chlorine, bromine or

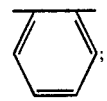

B and D together are a direct bond, $R^2$ and $R^3$ are the same or different and mean hydrogen or an organic acid radical with 1–15 C atoms;

$R^1$ and $R^2$ together are a carbonyl group;

$R^4$ is a hydrogen atom, $C_{1-10}$ alkyl, which can optionally be substituted by chlorine or bromine, cycloalkyl with 3–10 C atoms, an aryl radical with 6–10 C atoms optionally substituted by 1–3 chlorine, bromine, phenyl, $C_{1-4}$ alkyl, $C_{1-4}$ alkoxy, chloromethyl, fluoromethyl, trifluoromethyl, carboxy or hydroxy or a 5–6-member aromatic heterocyclic radical with at least 1 heteroatom, and if $R^5$ means a hydrogen atom, their salts with physiologically compatible bases and their cyclodextrin clathrates.

Groups $OR^2$ and $OR^3$ can be in alpha-position or beta-position. Formula I comprises both racemates and the possible pure diastereomers and enantiomers.

As alkyl groups $R^5$, straight-chain or branched-chain alkyl groups with 1–10 C atoms, such as, for example, methyl, ethyl, propyl, butyl, isobutyl, tert-butyl, pentyl, neopentyl, hexyl, heptyl, decyl, are suitable. The alkyl groups $R^5$ can optionally be substituted one or more times by halogen atoms, alkoxy groups, optionally substituted aryl or aroyl groups with 6–10 C atoms (substitution s. under aryl $R^5$), dialkylamino and trialkylammonium with 1-C atoms in the alkyl portion, in which case the simple substitution is to be preferred. As substituents, for example, there can be mentioned fluorine, chlorine or bromine, phenyl, dimethylamine, diethylamine, methoxy, ethoxy. As preferred alkyl groups $R^5$, those with 1–4 C atoms can be mentioned.

As aryl groups $R^5$, both substituted and unsubstituted aryl groups with 6–10 C atoms are suitable, such as, for example, phenyl, 1-naphthyl and 2-naphthyl, which can be respectively substituted by 1–3 halogen atoms (F, Cl, Br), a phenyl group, 1–3 alkyl groups with 1–4 C atoms each, a chloromethyl group, fluoromethyl group, trifluoromethyl group, carboxyl group, hydroxy group or alkoxy group with 1–4 C atoms. Preferred substituents in 3- and 4-position in the phenyl ring are, for example, fluorine, chlorine, alkoxy or trifluoromethyl, but in 4-position hydroxy.

The cycloalkyl group $R^5$ can contain in the ring 3–10 carbon atoms, preferably 5 and 6 carbon atoms. The rings can be substituted by alkyl groups with 1–4 carbon atoms. For example, there can be mentioned cyclopentylhexyl, cyclohexyl, methylcyclohexyl.

As heterocyclic groups $R^5$, 5- and 6-member aromatic heterocycles, which contain at least 1 heteroatom, preferably nitrogen, oxygen or sulfur, are suitable. For example, there can be mentioned 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, 2-tetrazolyl, i.a.

As acid radical $R^6$, physiologically compatible acid radicals are suitable. Preferred acids are organic carboxylic acids and sulfonic acids with 1-15 carbon atoms, which belong to the aliphatic, cycloaliphatic, aromatic, aromatic-aliphatic and heterocyclic series. These acids can be saturated, unsaturated and/or polybasic and/or substituted in the usual way. As examples for the substituents, there can be mentioned $C_{1-4}$ alkyl groups, hydroxy groups, $C_{1-4}$ alkoxy group, oxo groups or amino groups or halogen atoms (F, Cl, Br). For example, the following carboxylic acids can be mentioned: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, benzoic acids substituted with halogen (F, Cl, Br) or trifluoromethyl groups, hydroxy groups, $C_{1-4}$ alkoxy groups or carboxy groups, nicotinic acid, isonicotinic acid, 2-furancarboxylic acid, cyclopentylpropionic acid. As especially preferred acyl radicals and alkanesulfonyl radicals, those with up to 10 carbon atoms are suitable. As sulfonic acids, for example, methanesulfonic acid, ethanesulfonic acid, isopropanesulfonic acid, beta-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(beta-chloroethyl)aminosulfonic acid, N,N-diiosbutylaminosulfonic acid, N,N-dibutylaminosulfonic acid, pyrrolidino-, piperidino-, piperazino-, N-methylpiperazino- and morpholino-sulfonic acid are suitable.

As alkyl groups $R^4$, straight-chain and branched-chain, saturated and unsaturated alkyl radicals, preferably saturated, with 1-14, especially 1-10 C atoms are suitable, which optionally can be substituted by optionally substituted phenyl (substitution see under aryl $R^5$). For example, there can be mentioned the methyl, ethyl, propyl, butyl, isobutyl, tert-butyl, pentyl, hexyl, heptyl, octyl, butenyl, isobutenyl, propenyl, pentenyl, benzyl, m- and p-chlorobenzyl groups. If alkyl groups $R_4$ are halogen-substituted, fluorine, chlorine and bromine are suitable as halogens.

As an example for halogen-substituted alkyl groups $R^4$, alkyls with terminal trifluoromethyl groups are suitable.

The cycloalkyl group $R^4$ can contain in the ring 3-10 carbon atoms, preferably 3-6 carbon atoms. The rings can be substituted by alkyl groups with 1-4 carbon atoms. For example, there can be mentioned cyclopropyl, cyclobutyl, cyclopentyl, cyclohexyl, methylcyclohexyl.

As substituted or unsubstituted aryl groups $R^4$ for example, phenyl, 1-naphthyl and 2-naphthyl, which can each be substituted by 1-3 halogen atoms, a phenyl group, 1-3 alkyl groups each with 1-4 C atoms, a chloromethyl group, fluoromethyl group, trifluoromethyl group, carboxyl group, $C_1$-$C_4$ alkoxy group or hydroxy group, are suitable. The substitution in 3- and 4-position in the phenyl ring is preferred, for example, by fluorine, chlorine, alkoxy or trifluoromethyl or in 4-position by hydroxy.

As heterocyclic aromatic groups $R^4$, 5- and 6-member heterocycles that contain at least 1 heteroatom, preferably nitrogen, oxygen or sulfur, are suitable. For example, there can be mentioned 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, i.a.

As alkylene group B, straight-chain or branched-chain, saturated or unsaturated alkylene radicals, preferably saturated with 1-10 C atoms, especially with 1-5 C atoms, which optionally can be substituted by fluorine atoms, are suitable. For example, there can be mentioned: methylene, fluoromethylene, difluoromethylene, ethylene, 1,2-propylene, ethylethylene, trimethylene, tetramethylene, pentamethylene, 1,2-difluoroethylene, 1-fluoroethylene, 1-methyltetramethylene, 1-methyl trimethylene, 1-methylene-ethylene, 1-methylene-tetramethylene.

Alkylene group B can further constitute group

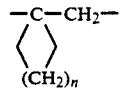

in which case n = 1-3, preferably 2-3.

As acid radicals $R^2$ and $R^3$, physiologically compatible acid radicals are suitable. Preferred acids are organic carboxylic acids and sulfonic acids with 1-15 carbon atoms, which belong to the aliphatic, cycloaliphatic, aromatic, aromatic-aliphatic or heterocyclic series. These acids can be saturated, unsaturated and/or polybasic and/or substituted in the usual way. As examples for the substituents, there can be mentioned $C_{1-4}$ alkyl, hydroxy, $C_{1-4}$ alkoxy, oxo or amino groups or halogen atoms (F, Cl, Br).

For example, the following carboxylic acids can e mentioned: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopentylacetic acid, cyclohexylacetic acid, cyclohexanecarboxylic acid, phenylacetic acid, phenoxyacetic acid, methoxyacetic acid, ethoxyacetic acid, mono-, di- and tri-chloroacetic acid, aminoacetic acid, diethylaminoacetic acid, piperidinoacetic acid, morpholinoacetic acid, lactic acid, succinic acid, adipic acid, benzoic acid, benzoic acids substituted with halogen (F, Cl, Br), trifluoromethyl, hydroxy, $C_{1-4}$ alkoxy or carboxy groups, nicotinic acid, isonicotinic acid, 2-furancarboxylic acid, cyclopentylpropionic acid. As especially preferred acid radicals $R^2$ and $R^3$, acyl radicals with up to 10 carbon atoms are suitable.

$R^2$ as a $C_{1-5}$ alkyl manes straight-chain or branched-chain alkyl radicals such as those which have already been mentioned for $R^4$ and $R^5$. Preferred alkyl radicals $R^7$ are methyl, ethyl, propyl and isopropyl.

Inorganic and organic bases are suitable for salt formation, as they are known to one skilled in the art for forming physiologically compatible salts. For example, there can be mentioned alkali hydroxides, such as sodium hydroxide and potassium hydroxide, alkaline earth hydroxides, such as calcium hydroxide, ammonia, amines, such as ethanolamine, diethanolamine, triethanolamine, n-methylglucamine, morpholine, tris(hydroxymethyl)methylamine, etc.

Preferred compounds of this invention are compounds of formula I, in which the radicals have the following meaning:

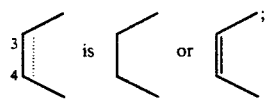

$R^1$ is $CH_2OH$, $COOR^5$ with $R^5$ meaning a hydrogen atom, an alkyl radical with 1-10 C atoms, a cycloalkyl radical with 5-6 C atoms, a phenyl radical optionally substituted by 1-2 chlorine, bromine, phenyl, $C_{1-4}$ alkyl, $C_{1-4}$ alkoxy, chloromethyl, fluoromethyl, trifluoromethyl, carboxy or hydroxy, or $R^1$ is $CONHR^6$ with $R^6$ meaning an alkanoyl radical or an alkanesulfonyl radical with 1-10 C atoms or radical $R^5$;

A is a trans, trans—CH=CH—CH=CH— group or a tetramethylene group;

B is a straight-chain or branched chain, saturated or unsaturated alkylene group with up to 10 C atoms which can optionally be substituted by fluorine, or the group

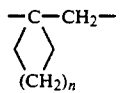

with n=1-3;

D is a direct bond, oxygen, sulfur, a —CH≡C group or a —CH=CR$^7$ group with R$^7$ as hydrogen, $C_{1-5}$ alkyl, chlorine, bromine or

B and D together are a direct bond, $R^2$ and $R^3$ are the same or different and mean hydrogen or an organic acid radical with 1-15 C atoms;

$R^1$ and $R^2$ together are a carbonyl group;

$R^4$ is a hydrogen atom, $C_{1-10}$ alkyl, cycloalkyl with 5-6 C atoms, a phenyl radical optionally substituted by 1-2 chlorine, bromine, phenyl, $C_{1-4}$ alkyl, $C_{1-4}$ alkoxy, chloromethyl, fluoromethyl, trifluoromethyl, carboxy or hydroxy, and if $R^5$ means a hydrogen atom, their salts with physiologically compatible bases and their cyclodextrin clathrates.

Especially preferred compounds of this invention are compounds of formula I, in which the radicals have the following meaning:

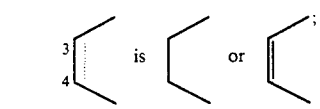

$R^1$ is $CH_2OH$, $COOR^5$ with $R^5$ meaning a hydrogen atom, an alkyl radical with 1-4 C atoms;

A is a trans, trans—CH=CH—CH=CH— group or a tetramethylene group;

B is a straight-chain or branched-chain alkylene group with up to 5 C atoms;

D is a direct bond or a —C≡C group or a —CH=CR$^7$ group with R$^7$ as hydrogen or $C_{1-5}$ alkyl or

B and D together are a direct bond, $R^2$ and $R^3$ are the same or different and mean hydrogen or an organic acid radical with 1-6 C atoms;

$R^1$ and $R^2$ together are a carbonyl group;

$R^4$ is a hydrogen atom or a $C_{1-10}$ alkyl, and if $R^5$ means a hydrogen atom, their salts with physiologically compatible bases and their cyclodextrin clathrates.

The invention further relates to a process for the production of the compounds of formula I according to the invention, which is characterized in that an aldehyde of formula II,

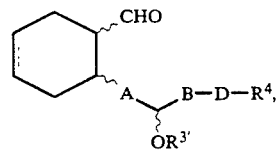

in which A, B, D, and R$^4$ have the above-indicated meaning, and R$^{3'}$ means silyl protecting groups, as then are mentioned for R$^8$, optionally after protection of free hydroxy groups with a magnesium organic compound of formula III,

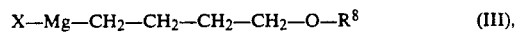

$$X\text{—Mg—}CH_2\text{—}CH_2\text{—}CH_2\text{—}CH_2\text{—O—}R^8 \qquad (III),$$

in which X means chlorine, bromine or iodine and R$^8$ means an easily cleavable ether radical, is reacted and then optionally separated into any sequence of isomers, protected hydroxy groups are released and/or a free hydroxy group is esterified and/or the 1-hydroxy group is oxidized to carboxylic acid and/or double bonds are hydrogenated and/or an esterified carboxyl group ($R^1 = COOR^5$) is saponified and/or reduced and/or a carboxyl group $R^5 = H$) is esterified and/or a free carboxy group ($R^5 \leq H$) is converted to an amide ($R^1 = CONHR^6$) or a carboxyl group with a physiologically compatible base is converted to a salt.

As ether radicals R$^8$ and R$^{3'}$ in the compound of formulas II and III, the radicals familiar to one skilled in the art are suitable. Easily cleavable ether radicals, such as, for example, dimethyl-tert-butylsilyl, trimethylsilylethyl, tribenzylsilylethyl, diphenyl-tert-butylsilylethyl, tetrahydropyranylethyl, tetrahydrofuranylethyl and alpha-ethoxyethyl are preferred, to mention only a few.

The reaction of the compound of formula II with an organometallic compound of formula III takes place in a way known in the art in an inert solvent or solvent mixture, such as, for example, diethyl ether, tetrahydrofuran, dioxane, toluene, dimethoxyethane, preferably diethyl ether or tetrahydrofuran. The reaction is performed at temperatures between −100° C. and 60° C., preferably at −78° C. to 0° C.

The production of the compound of formula III needed for this reaction takes place by the reaction of the corresponding hydroxyhalide by etherification with dihydropyran and p-toluenesulfonic acid and then reaction with magnesium.

The reduction to the compounds of formula I with $R^1$ meaning a $CH_2$—OH group is performed with a reducing agent suitable for the reduction of esters or carboxylic acids, such as, for example, lithium aluminum hydride, diisobutyl aluminum hydride, etc. As solvents, diethyl ether, tetrahydrofuran, dimethoxyethane, toluene, etc. are suitable. The reduction is performed at temperatures of −30° C. up to the boiling temperature of the solvent used, preferably 0° C. to 30° C.

The esterification of the alcohols of formula I ($R^2$=H and/or $R^3$=H) takes place in a way known in the art. For example, the esterification takes place in than an acid derivative, preferably an acid halide or an acid anhydride, is reacted in the presence of a base such as, for example, NaH, pyridine, triethylamine, tributylamine or 4-dimethylaminopyridine with an alcohol of formula I. The reaction can be performed without a solvent or in an inert solvent, preferably acetone, acetonitrile, dimethylacetamide, DMSO at temperatures above or below room temperature, for example between −80° C. to 100° C., preferably at room temperature.

The oxidation of the 1-hydroxy group is performed according to methods known to one skilled in the art. As oxidizing agents, for example, pyridinium dichromate (Tetrahedron Letters, 1979, 399), Jones reagent (J. Chem. Soc., 1953, 2555) or platinum/oxygen (Adv. In carbohydrate Chem. 17, 169 (1962)) or Collins oxidation and then Jones oxidation can be used. The oxidation with pyridinium dichromate is performed at temperatures of 0° C. to 100° C., preferably 20° C. to 40° C. in a solvent inert toward the oxidizing agent, for example, dimethylformamide.

The oxidation with Jones reagent is performed at temperatures of −40° C. to +40° C., preferably 0° C. to 30° C. in acetone as a solvent.

The oxidation with platinum/oxygen is performed at temperatures of 0° C. to 60° C. preferably 20° C. to 40° C. in a solvent inert toward the oxidizing agent such as, e.g. ethyl acetate.

The saponification of the esters of formula I is performed according to methods known to one skilled in the art, such as, for example, with basic catalysts. The compounds of formula I can be separated by the usual separation methods into the optical isomers.

The release of the functionally modified hydroxy groups takes place according to known methods. For example, the cleavage of hydroxy protecting groups, such as, for example, the tetrahydropyranyl radical, is performed in an aqueous solution of an organic acid, such as, e.g., oxalic acid, acetic acid, propionic acid, i.a., or in an aqueous solution of an inorganic acid such as e.g., hydrochloric acid. To improve the solubility, a suitably water-miscible inert organic solvent is added. Suitable organic solvent are, e.g., alcohols, such as methanol and ethanol, and ethers, such as dimethoxyethane, dioxane and tetrahydrofuran. Tetrahydrofuran is preferably used. The cleavage is performed preferably at temperatures between 20° C. and 80° c. The cleavage of the silyl ether protecting groups takes place, for example, with tetrabutylammonium fluoride or with potassium fluoride in the presence of a crown ether. As a solvent, for example, tetrahydrofuran, diethyl ether, dioxane, methylene chloride, etc., are suitable. The cleavage is performed preferably at temperatures between 0° C. and 80° C.

The saponification of the acyl groups takes place, for example, with alkali or alkaline-earth carbonates or hydroxides in an alcohol or in the aqueous solution of an alcohol. As an alcohol, aliphatic alcohols are suitable, such as e.g., methanol, ethanol, butanol, etc., preferably methanol. As alkali carbonates and hydroxides, potassium salts and sodium salts can be mentioned. The potassium salts are preferred.

As alkaline-earth carbonates and hydroxides, for example, calcium carbonate, calcium hydroxide and barium carbonate are suitable. The reaction takes place at −10° C. to +70° c., preferably at +25° C.

The introduction of the ester group

for $R^1$, in which $R^5$ represents an alkyl group with 1–10 C atoms, takes place according to methods known to one skilled in the art. The 1-carboxyl compounds are reacted, for example, with diazohydrocarbons in a way known in the art. The esterification with diazohydrocarbons takes place, e.g., in that a solution of the diazohydrocarbon in an inert solvent, preferably in diethyl ether, is mixed with the 1-carboxy compound in the same or in another inert solvent, such as, e.g., methylene chloride. After completion of the reaction in 1 to 30 minutes, the solvent is removed and the ester is purified in the usual way. Diazoalkanes are either known or can be produced according to known methods [Org. Reactions Vol., 8, pages 389–394 (1954)].

The introduction of the ester group

for $R^1$, in which $R^2$ represents a substituted or unsubstituted aryl group, takes place according to methods known to one skilled in the art. For example, the 1-carboxy compounds with the corresponding arylhydroxy compounds in an inert solvent are reacted with dicyclohexylcarbodiimide in the presence of a suitable base, for example, pyridine, DMAP, triethylamine. As a solvent, methylene chloride, ethylene chloride, chloroform, ethyl acetate, tetrahydrofuran, preferably chloroform, are suitable. The reaction is performed at temperatures between −30° C. and +50° C., preferably at 10° C.

If C=C double bonds contained in the primary product are to be reduced, the hydrogenation takes place according to methods known in the art.

The hydrogenation of the delta$^{8,10}$-diene system is performed, in a way known in the art, at low temperatures, preferably at about −20° C. to +30° C. in a hydrogen atmosphere in the presence of a noble metal catalyst. As a catalyst, for example, 10% palladium on carbon is suitable.

The leukotriene-B$_4$ derivatives of formula I with R$^1$ meaning a COOH group can be converted to a salt with suitable amounts of the corresponding inorganic bases with neutralization. For example, during dissolving of the corresponding acids in water, which contains the stoichiometric amount of the base, the solid inorganic salt is obtained after the evaporating off of the water or after the addition of a water-miscible solvent, e.g., alcohol or acetone.

For the production of an amine salt, the LTB$_4$ acid, e.g., is dissolved in a suitable solvent, for example, ethanol, acetone, diethyl ether, acetonitrile or benzene, and at least the stoichiometric amount of the amine is added to this solution. In this way, the salt usually accumulates in solid form or is isolated after evaporation of the solvent in the usual way.

The introduction of the amide group

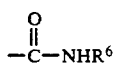

for R$^1$ takes place according to methods known to one skilled in the art. The carboxylic acids of formula I (R$^5$=H) are first converted in the presence of a tertiary amine, such as, for example, triethylamine, with chloroformic acid isobutyl ester to the mixed anhydride. The reaction of the mixed anhydride with the alkali salt of the corresponding amide or with ammonia (R$^6$=H) takes place in an inert solvent or solvent mixture, such as, for example, tetrahydrofuran, dimethoxyethane, dimethylformamide, hexamethylphosphoric acid triamide, at temperatures between −30° C. and +60° C., preferably at 0° C. to 30° C.

Another possibility for the introduction of the amide group

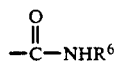

for R$^1$ is in the reaction of a 1-carboxylic acid of formula I (R$^5$=H), in which free hydroxy groups optionally are protected intermediately with compounds of formula IV,

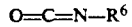  (IV), in which R$^6$ has the above indicated meaning.

The reaction of the compound of formula I (R$^5$≦H) with an isocyanate of formula IV optionally takes place with the addition of a tertiary amine, such as, e.g., triethylamine or pyridine. The reaction can be performed without a solvent or in an inert solvent, preferably acetonitrile, tetrahydrofuran, acetone, dimethylacetamide, methylene chloride, diethyl ether, toluene, at temperatures between −80° C. to 100° C., preferably at 0° C. to 30° c.

If the initial product contains OH groups in the leukotriene-B$_4$ radical, these OH groups are also reacted. Finally, if end products are desired which contain free hydroxyl groups, a start is suitably made from the initial products, in which these are intermediately protected by preferably easily cleavable ether or acyl radicals.

The separation of enantiomers and/or diastereomers takes place according to methods known to one skilled in the art., e.g., by chromatographic methods, for example, high-pressure liquid chromatography on optically active supply materials.

The compounds of formula II used as initial material can be produced, for example, by 2-hydroxymethylbenzyl alcohol being converted to the monosilyl ether of formula V in a way known in the art.

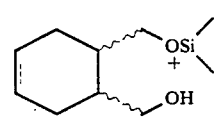  (V)

By oxidation, e.g., with Collins reagent or by the Swern process, the aldehyde of formula VI is obtained,

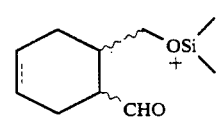  (VI)

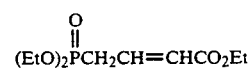  (VII)

which is converted in a Wittig-Horner olefinization with the phosphonate of formula VII and a base and optionally subsequent hydrogenation to the ester of formula VIII, in which A

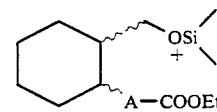  (VIII)

has the above-indicated meaning. As bases, for example, potassium-tert-butylate, diazabicyclononane or sodium hydride are suitable. The reduction of the ester group, for example, with DIBAH and then oxidation of the primary alcohol obtained, e.g., with manganese dioxide or Collins reagent, results in the aldehyde of formula IX

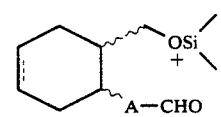  (IX)

The organometallic reaction of the aldehyde of formula IX with a Grignard reagent of formula X, in which B, D

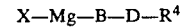  (X)

and R$^4$ exhibit the above-indicated meanings and X means chlorine, bromine or iodine, results after protection of the hydroxy group and optionally diastereomer separation (for example by acylation) in the compounds of formula XI

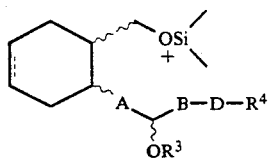

(XI)

The production of the compound of formula X needed for the organometallic reaction takes place by the reaction of the corresponding terminal halide with magnesium. By reaction of silyl ether XI with tetrabutylammonium fluoride, the alcohol of formula XII is obtained.

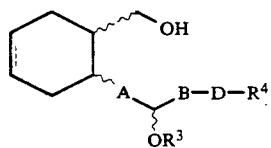

(XII)

The oxidation of the primary alcohol group in XII, e.g., with Collins reagent or pyridinium dichromate, results in the aldehyde of formula II.

In the compounds of formula XI, in which B means a $CH_2$ group and D means a $-C\equiv C-$ group or a $CH=CR^7$ group, a propargyl halide can be attained, for example by an organometallic reaction, with the aldehyde of formula IX and subsequent alkylation with a corresponding alkyl halide and optionally subsequent Lindlar hydrogenation.

The compounds of formula I act in an anti-inflammatory and anti-allergic manner. In addition, they have antimycotic properties. Consequently, the new leukotriene-$B_4$ derivatives of formula I represent valuable pharmaceutical active ingredients. The compounds of formula I are especially suitable for topical application, since they exhibit a dissociation between desirable topical effectiveness and undesirable systemic side effects.

The new leukotriene-$B_4$ derivatives of formula 1 are suitable in combination with the auxiliary agents and vehicles usual in galenic pharmaceutics for topical treatment of contact dermatitis, eczemas of the most varied types, neurodermatoses, erythrodermia, burns, tinea, pruritus vulvae, pruritus ani, rosacea, lupus erythematosus cutaneus, psoriasis, lichen ruber planus and verrucosis and similar skin diseases.

The production of pharmaceutical agent specialties takes place in the usual way, by the active materials with suitable additions being converted into the desired form of application such as, for example: solutions, lotions, ointments, creams or plasters.

In the pharmaceutical agents thus formulated, the active ingredient concentration is dependent on the form of application. In lotions and ointments, an active ingredient concentration of 0.0001% to 1% is preferably used.

Further, the new compounds optionally in combination with the usual vehicles and auxiliary agents are also very suitable for the production of inhalants, which can be used for the treatment of allergic diseases of the respiratory system such as, for example, bronchial asthma or rhinitis.

Further, the new leukotriene-$B_4$ derivatives also are suitable in the form of capsules, tablets or coated tablets, which preferably contain 0.1 to 100 mg of active ingredient or are applied orally in the form of suspensions, which preferably contain 1–200 mg of active ingredient per dosage unit, and are also applied rectally to treat allergic diseases of the intestinal tract, such as colitis ulcerosa and colitis granulomatosa.

The new leukotriene-$B_4$ derivatives can also be used combined with, e.g., lipoxygenase inhibitors, cyclooxygenase inhibitors, prostacyclin agonists, thromboxane antagonists, leukotriene-$D_4$ antagonists, leukotriene-$E_4$ antagonists, leukotriene-$F_4$ antagonists, phosphodiesterase inhibitors, calcium antagonists or PAF antagonists.

EXAMPLE 1

(+)-(5RS)-5-Acetoxy-5-[cis-(6RS)-6-((1E,3E)-(5RS)-5-acetoxy-1,3,tridecadienyl)-(1RS)-3-cyclohexen-1-yl]-pentanol Nonpolar and Polar Diastereomers A solution of 16 g of 4-chloro-1-(tert-butyldimethylsilyloxy)-butane in 14.4 ml of tetrahydrofuran and 0.84 ml of dibromomethane is instilled in 4 g of magnesium at 25° C. under argon, heated for 10 minutes to 70° C., stirred for 30 minutes at 25° C. and diluted with 45.2 ml of tetrahydrofuran.

A solution of 4.2 g of cis-(1RS)-1-formyl-(6RS)-6-[(1E,3E)-(5RS)-5-acetoxy-1,3-tridecadienyl]-3-cyclohexene in 8.25 ml of tetrahydrofuran is installed in 29.9 ml of this magnesium organic solution at −20° C. under argon and stirred for 30 minutes at −20° C. It is mixed with 150 ml of saturated ammonium chloride solution, extracted three times with ether, the organic phase is shaken out with brine, dried on magnesium sulfate and concentrated by evaporation in a vacuum. The residue is chromatographed on silica gel. With hexane/ethyl acetate (8+2), 4.1 g of the alcohol is obtained as a colorless oil.

IR ($CHCl_3$): 3600, 2930, 2858, 1725, 1250, 992, 838 $cm^{-1}$.

For acetylation, 6.3 ml of acetic anhydride is added to a solution of 6 g of the above-described alcohol in 38 ml of pyridine and stirred for 16 hours at 24° C. Then, it is concentrated by evaporation in a vacuum with adding toluene and the residue is chromatographed on silica gel. With hexane/ethyl acetate (95+5), 4.9 g of the acetate is obtained as a colorless oil.

IR: 2930, 2860, 1728, 1255, 991, 838 $cm^{-1}$.

For cleavage of the protecting groups, 4.55 g of the above-produced acetate in 320 ml of tetrahydrofuran is stirred with 7.5 g of tetrabutylammonium fluoride for 1 hour at 20° C. and for 4 hours at 24° C. under argon. Then, it is diluted with ether, washed three times with water, dried on magnesium sulfate and concentrated by evaporation in a vacuum. The residue is chromatographed with hexane/ethyl acetate (6+4) on silica gel. In this way, first 1.32 g of the nonpolar diastereomer and then 1.7 g of the polar diastereomers of the title compound are obtained as colorless oils.

IR (nonpolar diastereomer); 3630, 3430, 2930, 2860, 1728, 1608, 1375, 1250, 992 $cm^{-1}$.

IR (polar diastereomer); 3630, 3480, 2930, 2860, 1729, 1608, 1375, 1250, 992 $cm^{-1}$.

The initial material for the above-named title compound is produced as follows:

1a) 5-cis-1-(tert-Butyl-dimethylsilyloxymethyl)-3-cyclohexen-6-yl]-(2E,4E)-pentadienoic acid ethyl ester A solution of 25 g of cis-4-cyclohexene-1,2-dicarboxylic acid anhydride in 140 ml of tetrahydrofuran is instilled in a suspension of 10 g of lithium aluminum hydride in 140 ml of tetrahydrofuran at room temperature and the mixture is then stirred for 3 hours at reflux temperature. It is cooled to 0° C. a mixture of tetrahydrofuran/water (1+1) is instilled slowly, stirred for 30 minutes, mixed with 150 ml of chloroform, filtered and the filtrate is concentrated by evaporation in a vacuum. The residue is distilled at 0.2 mm/Torr and 150° C. on a bulb tube. After recrystallization of the distillate from toluene/pentane, 21 g of cis-1,6-dihydroxymethyl-3-cyclohexene is obtained as colorless crystals, melting point 33°–35° C.

19 g of tert-butyldimethylsilyl chloride is added to a solution of 17.7 g of the above-produced diol and 17.2 g of imidazole in 147 ml of dimethylformamide at 0° C. under argon and stirred for 16 hours at 25° C. It is diluted with 1.5 l of ether, shaken out twice with 100 ml of 10% sulfuric acid each time, washed neutral with brine, dried on magnesium sulfate and concentrated by evaporation in a vacuum. The residue is chromatographed on silica gel. With hexane/ethyl acetate (9+1), 16.2 g of cis-1-(tert-butyl-dimethylsilyloxymethyl)-6-hydroxymethyl)-3-cyclohexene is obtained as a colorless oil.

IR: 3580, 3390, 2930, 2858, 835 cm$^{-1}$.

140 g of Collins reagent (chromic acid-pyridine complex) is added to a solution of 14 g of the above-described monosilyl ether in 700 ml of methylene chloride at 0° C. and stirred for 40 minutes at 0° C. Then, it is diluted with a mixture of hexane/ether (3+2), Celite is added, filtered and concentrated by evaporation in a vacuum. The residue is chromatographed with hexane/ethyl acetate (9+1) on silica gel. In this way, 12.8 g of cis-1-(tert-butyl-dimethylsilyloxymethyl)-6-formyl-3-cyclohexene is obtained as a colorless oil.

IR: 2930, 2860, 2730, 1715, 838 cm$^{-1}$.

For Wittig-Horner olefinization, 12.4 g of phosphonocrotonic acid triethyl ester and 6.3 g of diazabicycloundecene (DBU) are added at 24° C. to a stirred suspension of 2.1 g of lithium chloride in 412 ml of acetonitrile and stirred for 10 minutes. Then, a solution of 10.5 g of the above-described aldehyde is instilled in 83 ml of acetonitrile, stirred for 3 hours at 24° C. and then diluted with ether. It is shaken out in succession with water, 10% citric acid solution and water, dried on magnesium sulfate and concentrated by evaporation in a vacuum. The residue is chromatographed with hexane/ethyl acetate (95+5) on silica gel. In this way, 9 g of the title compound is obtained as a colorless oil.

IR: 2930, 2858, 1710, 1638, 1618, 1256, 1003, 940, 838 cm$^{-1}$.

1b) 5-[cis-1-(tert-Butyl-dimethylsilyloxymethyl)-3-cyclohexen-6-yl]-(2E,4E)-pentadien-1-al 41 ml of a 1.2 molar solution of diisobutyl aluminum hydride in toluene is instilled in a solution of 8.8 g of the ester, produced according to example 1a, in 200 ml of toluene at −70° C. under argon and stirred for 40 minutes at −70° C. Then, 4 ml of isopropanol and then 21 ml of water is instilled, stirred for 2 hours at 22° C. filtered, washed with methylene chloride and concentrated by evaporation in a vacuum. The residue is purified by chromatography on silica gel. With hexane/ethyl acetate (8+2), 7.1 g of the alcohol is obtained as a colorless oil.

IR: 3630, 3460, 838 cm$^{-1}$.

A solution of 7.1 g of the above-produced alcohol in 260 ml of methylene chloride is mixed with 20 g of manganese dioxide and stirred for 4 hours at 24° C. Then, it is filtered, concentrated by evaporation and chromatographed on silica gel. With hexane/ethyl acetate (85+15), 6.2 g of the title compound is eluted as a colorless oil.

IR: 2930, 2860, 1680, 1638, 990, 950, 838 cm$^{-1}$.

1c) (5RS)-5-Acetoxy-1-[cis-1-(tert-butyl-dimethylsilyloxymethyl)-3-cyclohexen-6-yl]-(1E,3E)-tridecadiene A solution of 7.95 ml of octyl bromide in 12 ml of ether is instilled in 1.2 g of magnesium in 5 ml of ether with heating and stirred for 30 minutes at 25° C.

A solution of 3.0 g of the aldehyde, produced according to example 1b, in 48 ml of ether is installed in 5.85 ml (=10.77 mmol) of this Grignard solution at −20° C. under argon and stirred for 3 hours at −20° C. It is mixed with saturated ammonium chloride solution, extracted three times with ether, the organic phase is shaken out with brine, dried on magnesium sulfate and concentrated by evaporation in a vacuum. The residue is chromatographed on silica gel. With hexane/ethyl acetate (7+3), 3.35 g of the alcohol is eluted as a colorless oil.

IR: 3620, 3460, 2930, 2858, 992, 838.

For acetylation, 6 ml of acetic anhydride is added to a solution of 3.3 g of the above-produced alcohol in 12 ml of pyridine and stirred for 16 hours at 24° C. Then, it is concentrated by evaporation in a vacuum with the addition of toluene and the residue is chromatographed on silica gel. With hexane/ethyl acetate (8+21), 3.3 g of the title compound is obtained as an oil.

IR: 2930, 2858, 1730, 1254, 990, 838 cm$^{-1}$.

1c) (5RS)-5-Acetoxy-1-[cis-1-(tert-butyl-dimethylsilyloxymethyl)-3-cyclohexen-6-yl]-(1E,3E)-tridecadiene A solution of 7.95 ml of octyl bromide in 12 ml of ether is instilled in 1.2 g of magnesium in 5 ml of ether with heating and stirred for 30 minutes at 25° C.

A solution of 3.0 g of aldehyde, produced according to example 16, in 48 ml of ether is installed in 5.85 ml (=10.77 mmol) of this Grignard solution at −20° C. under argon and stirred for 3 hours at −20° C. It is mixed with saturated ammonium chloride solution, extracted three times with ether, the organic phase is shaken out with brine, dried on magnesium sulfate and concentrated by evaporation in a vacuum. The residue is chromatographed on silica gel. With hexane/ethyl acetate (7+3), 3.35 g of the alcohol is eluted as a colorless oil.

IR: 3620, 3460, 2930, 2858, 992, 838.

For acetylation, 6 ml of acetic anhydride is added to a solution of 3.3 g of the above-produced alcohol in 12 ml of pyridine and stirred for 16 hours at 24° C. Then, it is concentrated by evaporation in a vacuum with the addition of toluene and the residue is chromatographed on silica gel. With hexane/ethyl acetate (8+2), 3.3 g of the title compound is obtained as an oil.

IR: 2930, 2858, 1730, 1254, 990, 838 cm$^{-1}$.

1d) cis-1RS)-1-Formyl-(6RS)-6-[(1E,3E)-(5RS)-5-acetoxy-1,3-tridecadienyl]-3-cyclohexene 6.55 g of tetrabutylammonium fluoride is added to a solution of 3.2 g of the acetate, produced according to example 1c), in 320 ml of tetrahydrofuran at 0° C., stirred for 1 hour at 0° C. and for 3 hours at 24° C. Then, it is diluted with 1.2 l of ether and washed three times with brine. It is dried on magnesium sulfate, concentrated by evaporation in a vacuum, and the residue is chromatographed on silica gel. With hexane/ethyl acetate (6+4), 2.4 g of the alcohol is eluted as a colorless oil.

IR: 3620, 3460, 2930, 2860, 1722, 1250, 991 cm$^{-1}$.

19 g of Collins reagent (chromic acid-pyridine complex) is added to a solution of 2.71 g of the above-produced alcohol in 7 5ml of methylene chloride at 0° C. and stirred for 15 minutes at 0° C. Then, it is diluted with a mixture of hexane/ether (3+2), Celite is added, filtered and concentrated by evaporation in a vacuum. The aldehyde thus obtained is used without further purification.

EXAMPLE 2

(+)-(5RS)-5-Acetoxy-5-[cis-(6RS)-6-((1E,3E)-(5RS)-5-acetoxy-1,3-tridecadienyl)-(1RS)-3-cyclohexen-1-yl]-pentanoic Acid Diastereomer A 1.92 g of Collins reagent is added to a solution of 350 mg of the nonpolar diastereomeric diacetate, described in example 1, in 28 ml of methylene chloride at 0° C. and stirred for 15 minutes at 0° C. Then, it is diluted with a mixture of hexane/ether (3+2), Celite is added, filtered, washed with hexane/ether (3+2) and concentrated by evaporation in a vacuum.

0.7 ml of Jones reagent (J. Chem. Soc., 1953, 2555) is instilled in a solution of 360 mg of the above-produced aldehyde in 12.5 ml of acetone with stirring at −20° C. and stirred for 12 minutes at −20° C. under argon. Then, 3 ml of isopropanol is added, stirred for 10 minutes, diluted with 40 ml of ether, filtered, washed with ether, the ether phase is shaken out twice with brine, dried on magnesium sulfate and concentrated by evaporation in a vacuum. The residue is chromatographed on silica gel. With hexane/ethyl acetate (6+4), 290 mg of the title compound is obtained as a colorless oil.

IR: 3520 (broad), 2928, 2859, 1725, 1372, 1250, 991, 948 cm$^{-1}$.

EXAMPLE 3

(+)-(RS)-5-Hydroxy-5-[cis-(6RS)-6-((1E,3E)-(5RS)-5-hydroxy-1,3-tridecadienyl)-(1RS)-3-cyclohexen-1-yl]-pentanoic Acid Diastereomer A 60 mg of the nonpolar diastereomeric diacetate (diastereomer A) described in example 2 is stirred for 48 hours at 24° C. with 2.5 ml of a solution of potassium hydroxide in water and ethanol (production: 5 g of potassium hydroxide is dissolved in 67.5 ml of water and 182.5 ml of ethanol). Then, it is acidified with 10% citric acid solution to pH 4, extracted four times with 15 ml of methylene chloride each, the organic phase is shaken out with brine, dried on magnesium sulfate and concentrated by evaporation in a vacuum. The residue is chromatographed with ethyl acetate/hexane (8+2) on silica gel. In this way, 41 mg of the title compound is obtained as a colorless oil.

IR: 3600, 3400 (broad), 2930, 2859, 1720, 1375, 992 cm$^{-1}$.

EXAMPLE 4

(+)-(5RS)-5-Acetoxy-5-[cis-(6RS)-6-((1E,3E)-(5RS)-5-hydroxy-1,3-tridecadienyl)-(1RS)-3-cyclohexen-1-yl]-pentanoic Acid Diastereomer A 1.5 ml of a 0.5 normal sodium hydroxide solution is added to a solution of 70 mg of the nonpolar diastereomeric diacetate (diastereomer A), produced according to example 2, in 1.5 ml of methanol at 24° C. and stirred for 7 hours at 24° C. under argon. Then, it is diluted with 2 ml of water and acidified at ice bath temperature with 10% citric acid solution to pH 4. It is extracted four times with 30 ml of ethyl acetate each, the organic phase is shaken out with brine, dried on magnesium sulfate and concentrated by evaporation in a vacuum. The residue is chromatographed on silica gel. With ether/hexane (1+1), 51 mg of the title compound is obtained as a colorless oil.

IR: 3600, 3450, 2930, 2859, 1722, 1375, 1250, 992 cm$^{-1}$.

EXAMPLE 5

(30    )-(5RS)-5-Hydroxy-5-[cis-(6RS)-6-((1E,3E)-(5RS)-5-hydroxy-1,3-tridecadienyl)-(1RS)-3-cyclohexen-1-yl]-pentanol diastereomer A 88 mg of the nonpolar diastereomeric diacetate described in example 1 is stirred for 60 hours at 24° C. with 2.7 ml of a solution of potassium hydroxide in water and ethanol (production: 5 g of potassium hydroxide is dissolved in 67.5 ml of water and 182.5 ml of ethanol). Then, it is acidified with 10% citric acid solution to pH 6, extracted four times with 20 ml of methylene chloride each, the organic phase is shaken out with brine, dried on magnesium sulfate and concentrated by evaporation in a vacuum. The residue is chromatographed with ethyl acetate on silica gel. In this way, 48 mg of the title compound is obtained as a colorless oil.

IR: 3620, 3380 (broad), 2929, 2860, 992 cm$^{-1}$.

EXAMPLE 6

(+)-(5RS)-5-Acetoxy-5-[cis-(6RS)-6-((1E,3E)-(5RS)-5-hydroxy-1,3-tridecadienyl)-(1RS)-3-cyclohexen-1-yl]-pentanol Diastereomer A 58 mg of the nonpolar diastereomeric diacetate, described in example 1, in 1.4 ml of methanol is stirred for 4 hours at 24° C. with 1.4 ml of a 0.5 normal sodium hydroxide solution under argon. Then, it is diluted with 5 ml of water, neutralized with 10% citric acid solution, extracted four times with 20 ml of methylene chloride each, the organic phase is shaken out with brine, dried n magnesium sulfate and concentrated by evaporation in a vacuum. The residue is chromatographed with ethyl acetate/hexane (1+1) on silica gel. In this way, 21 mg of the title compound is obtained as a colorless oil.

IR: 3600, 3450 (broad), 2930, 2860, 1730, 1375, 1252, 993 cm$^{-1}$.

EXAMPLE 7

(+)-(5RS)-5-Acetoxy-5-[cis-(6RS)-6-((1E,3E)-(5RS)-5-acetoxy-1,3-tridecadienyl)-(1RS)-3-cyclohexen-1-yl]-pentanoic Acid Diastereomer B Analogously to example 2, 315 mg of the title compound is obtained as a colorless oil from 425 mg of the polar diastereomeric diacetate produced according to example 1.

IR: 3515 (broad), 2928, 2859, 1725, 1372, 1250, 991, 948 cm$^{-1}$.

EXAMPLE 8

(+)-(5RS)-5-Hydroxy-5-[cis-(6RS)-6-((1E,3E)-(5RS)-5-hydroxy-1,3-tridecadienyl)-(1RS)-3-cyclohexen-1-yl]-pentanoic Acid Diastereomer B Analogously to example 3, 240 mg of the title compound is obtained as a colorless oil from 320 mg of the diacetate (diastereomer B) produced according to example 7.

IR: 3600, 3420 (broad), 2930, 2860, 1720, 1375, 992 cm$^{-1}$.

EXAMPLE 9

(+)-(4RS)-5-Acetoxy-5-[cis-(6RS-6-((1E,3E)-(4RS)-5-hydroxy-1,3-tridecadienyl)-(1RS)-3-cyclohexen-1-yl]-pentanoic Acid Diastereomer B Analogously to example 4, 70 mg of the title compound is obtained as a colorless oil from 130 mg of the diacetate (diastereomer B) produced according to example 7.

IR: 3620, 3400 (broad), 2930, 2859, 1722, 1375, 1250, 992 cm$^{-1}$.

EXAMPLE 10

(+)-(5RS)-5-Hydroxy-5-[cis-(6RS)-6-((1E,3E)-(5RS)-5-hydroxy-1,3-tridecadienyl)-(1RS)-3-cyclohexen-1-yl]-pentanol Diastereomer B Analogously to example 5, 81 mg of the title compound is obtained as a colorless oil from 145 mg of the polar diastereomeric diacetate produced in example 1.

IR: 3600, 3400 (broad), 2930, 2860, 992 cm$^{-1}$.

EXAMPLE 11

(+)-(5RS)-5-Acetoxy-5-[cis-(6RS)-6-((1E,3E)-(5RS)-5-hydroxy-1,3-tridecadienyl)-(1RS)-3-cyclohexen-1-yl]-pentanol Diastereomer B Analogously to example 6, 40 mg of the title compound is obtained as a colorless oil from 70 mg of the polar diastereomeric diacetate produced in example 1.

IR: 3620, 3430 (broad), 2930, 2860, 1730, 1375, 1250, 993 cm$^{-1}$.

EXAMPLE 12

(+)-(5RS)-5-Acetoxy-5-[cis-(2RS)-2-((1E,3E)-(5RS)-5-acetoxy-1,3-tridecadienyl)-(1RS)-cyclohex-1-yl]-pentanol Nonpolar and Polar Diastereomers Analogously to example 1, 1.2 g of the nonpolar diastereomer and 1.3 g of the polar diastereomer of the title compound are obtained as colorless oils from 4 g of cis-(1RS)-1-formyl-(2RS)-2-[(1E,3E)-(5RS)-5-acetoxy-1,3-tridecadienyl]cyclohexane.

IR (nonpolar diastereomer); 3620, 3420, 2929, 2859, 1729, 1607, 1375, 1250, 992 cm$^{-1}$.

IR (polar diastereomer) 3600, 3430, 2929, 2860, 1729, 1607, 1375, 1250, 992 cm$^{-1}$.

The initial material for the above title compound is produced as follows:

12a) 5-[cis-1-(tert-Butyl-dimethylsilyloxymethyl)-cyclohex-2-yl]-(2E,4E)-pentadienoic Acid Ethyl Ester Analogously to example 1a), the title compound is obtained as a colorless oil from cis-1,2-dihydroxymethyl-cyclohexane.

IR: 2929, 2859, 1710, 1638, 1618, 1255, 1004, 940, 838 cm$^{-1}$.

12b) 5-[cis-1-(tert-Butyl-dimethylsilyloxymethyl)-cyclohex-2-yl]-(2E,4E)pentadien-1-al Analogously to example 1b), 13 g of the title compound is obtained as a colorless oil from 16 g of the ester produced according to example 12a).

IR: 2930, 2859, 1680, 1640, 992, 950, 840 cm$^{-1}$.

12c) (5RS)-5-Acetoxy-1-[cis-1-(tert-butyl-dimethyl-silyloxymethyl)-cyclohex-1-yl]-(1E,3E)-tridecadiene Analogously to example 1c), 3.8 g of the title compound is obtained as a colorless oil from 4.2 g of the aldehyde produced according to example 12b).

IR: 2928, 2859, 1730, 1255, 990 838 cm$^{-1}$.

12d) cis-(1RS)-1-Formyl-(2RS)-2-[(1E,3E)-(5RS)-5-acetoxy-1,3tridecadienyl]-cyclohexane Analogously to example 1d, 2.9 g of the aldehyde is obtained as crude produce from 4.2 g of the acetate produced according to example 12c).

EXAMPLE 13

(+)-(5RS)-5-Acetoxy-5-[cis-(2RS)-2-((1E,3E)-(5RS)-5-acetoxy-1,3-tridecadienyl)-(1RS)-cyclohex-1-yl]-pentanoic Acid Diastereomer A Analogously to example 2, 230 mg of the title compound is obtained as a colorless oil from 335 mg of the nonpolar diastereomeric diacetate produced according to example 12.

IR: 3520 (broad), 2930, 2860, 1725, 1373, 1251, 991, 948 cm$^{-1}$.

EXAMPLE 14

(+)-(5RS)-5-Hydroxy-5-[cis-(2RS)-2-((1E,3E)-(5RS)-5-hydroxy-1,3-tridecadienyl)-(1RS)-cyclohex-1-yl]-pentanoic Acid Diastereomer A Analogously to example 3, 253 mg of the title compound is obtained as a colorless oil from 390 mg of the diacetate (diastereomer A) produced according to example 13.

IR: 3600, 3410 (broad), 2930, 2860, 1720, 1375, 993 cm$^{-1}$.

EXAMPLE 15

(+)-(5RS)-5-Acetoxy-5-[cis-(2RS)-2-((1E,3E)-(5RS)-5-hydroxy-1,3-tridecadienyl)-)1RS)-cyclohex-1-yl]-pentanoic Acid Diastereomer A Analogously to example 4, 77 mg of the title compound is obtained as a colorless oil from 110 mg of the diacetate (diastereomer A) produced according to example 13.

IR: 3600, 3430, 2929, 2858, 1722, 1375, 1250, 992 cm$^{-1}$.

EXAMPLE 16

(+)-(5RS)-5-Acetoxy-5-[cis-(2RS)-2-((1E,3E)-(5RS)-5-acetoxy-1,3-tridecadienyl)-(1RS)-cyclohex-1-yl]-pentanoic Acid Diastereomer B Analogously to example 2, 190 mg of the title compound is obtained as a colorless oil from 270 mg of the polar diastereomeric diacetate produced according to example 12.

IR: 3600 (broad), 2930, 2859, 1725, 1375, 1250, 991, 948 cm$^{-1}$.

EXAMPLE 17

(+)-(5RS)-5-Hydroxy-5-[cis-(2RS)-2-((1E,3E)-(5RS)-5-hydroxy-1,3-tridecadienyl)-(1RS)-cyclohex-1-yl]-pentanoic Acid Diastereomer B Analogously to example 3, 185 mg of the title compound is obtained as a colorless oil from 280 mg of the diacetate (diastereomer B) produced according to example 16.

IR: 3610, 3415 (broad), 2930, 2860, 1720, 1375, 993 cm$^{-1}$.

EXAMPLE 18

(+)-(5RS)-5-Acetoxy-5-[cis-(2RS)-2-((1E,3E)-(5RS)-5-hydroxy-1,3-tridecadienyl)-(1RS)-cyclohex-1-yl]-pentanoic Acid Diastereomer B Analogously to example 4, 80 mg of the title compound is obtained as a colorless oil from 140 mg of the diacetate (diastereomer B) produced according to example 16.

IR: 3600, 3420, 2930, 2859, 1722, 1376, 1251, 992 cm$^{-1}$.

EXAMPLE 19

(+)-(5RS)-5-Acetoxy-5-[cis-(6RS)-6-((1E,3E)-(5RS)-5-acetoxy-1,3-tridecadienyl)-(1RS)-3-cyclohexen-1-yl]-pentanoic Acid Methyl Ester Diastereomer A An ethereal diazomethane solution is instilled until permanent yellow coloring in a solution of 51 mg of the acid, produced according to example 2, in 5 ml of methylene chloride at 0° C. and stirred for 15 minutes at 0° C. Then, it is concentrated by evaporation in a vacuum and the residue is chromatographed on silica gel. With hexane/ethyl acetate (9+1), 48 mg of the title compound is obtained as a colorless oil.

IR (film): 2923, 2851, 1739, 1655, 1370, 1240, 990 cm$^{-1}$.

EXAMPLE 20

(+)-(5RS)-5-Hydroxy-5-[cis-(6RS)-6-((1E,3E)-(5RS)-5-hydroxy-1,3-tridecadienyl)-(1RS)-3-cyclohexen-1-yl]-pentanoic Acid Methyl Ester Diastereomer A An ethereal diazomethane solution is instilled until permanent yellow coloring in a solution of 40 mg of the acid, produced according to example 3, in 4 ml of methylene chloride at 0° C. and stirred for 15 minutes at 0° C. Then, it is concentrated by evaporation in a vacuum, and the residue is chromatographed on silica gel. With hexane/ethyl acetate (1+9), 32 mg of the title compound is obtained as a colorless oil.

IR (film): 3610, 2922, 2853, 1737, 1655, 1435, 990 cm$^{-1}$.

EXAMPLE 21

(+)-(5RS)-5-Acetoxy-5-[cis-(6RS)-6-((1E,3E)-(5RS)-5-hydroxy-1,3-tridecadienyl)-(1RS)-3-cyclohexen-1-yl]-pentanoic Acid Methyl Ester Diastereomer A An ethereal diazomethane solution is instilled until permanent yellow coloring in a solution of 38 mg of the acid, produced according to example 4, in 4 ml of methylene chloride at 0° C. and stirred for 15 minutes at 0° C. Then, it is concentrated by evaporation in a vacuum, and the residue is chromatographed on silica gel. With hexane/ethyl acetate (1+1), 30 mg of the title compound is obtained as a colorless oil.

IR (film): 3420, 2923, 2858, 1739, 1655, 1370, 1240, 990 cm$^{-1}$.

EXAMPLE 22

(+)-(5RS)-5-Acetoxy-5-[cis-(2RS)-2-((1E,3E)-(5RS)-5-acetoxy-1,3-tridecadienyl)-(1RS)-cyclohex-1-yl]-pentanoic Acid Methyl Ester Diastereomer A Analogously to example 19, 71 mg of the title compound is obtained as a colorless oil from 85 mg of the acid produced according to example 13.

IR (film): 2924, 2852, 1739, 1655, 1371, 1240, 991 cm$^{-1}$.

EXAMPLE 23

(+)-(5RS)-5-Hydroxy-5-[cis-(2RS)-2-((1E,3E)-(5RS)-5-hydroxy-1,3-tridecadienyl)-(1RS)-cyclohex-1-yl]-pentanoic Acid Methyl Ester Diastereomer A Analogously to example 20, 65 mg of the title compound is obtained as a colorless oil from 73 mg of the acid produced according to example 14.

IR (film): 3600, 2922, 2852, 1738, 1655, 1436, 991 cm$^{-1}$.

EXAMPLE 24

(+)-(5RS)-5-Acetoxy-5-[cis-(2RS)-2-((1E,3E)-(5RS)-5-hydroxy-1,3-tridecadienyl)-(1RS)-cyclohex-1-yl]-pentanoic Acid Methyl Ester Diastereomer A Analogously to example 21, 40 mg of the title compound is obtained as a colorless oil from 45 mg of the acid produced according to example 15.

IR (film): 3430, 2924, 2859, 1739, 1655, 1370, 1240, 990 cm$^{-1}$.

EXAMPLE 25

(+)-(5RS)-5-Hydroxy-5-[cis-(6RS)-6-((1E,3E)-(5RS)-5-hydroxy-1,3-tridecadienyl)-(1RS)-3-cyclohexen-1-yl]-pentanoic Acid-1,5-lactone Diastereomer A 1 g of anhydrous magnesium sulfate is added in portions to a solution of 40 mg of the acid, produced according to example 3, in 8 ml of toluene at 24° C. over a period of 24 hours and stirred for another 24 hours at 24° C. Then, it is filtered and the evaporation residue is chromatographed on silica gel. With toluene/ethyl acetate (7+3), 22 mg of the lactone is eluted as a colorless oil.

IR (CHCl$_3$): 3600, 2930, 2860, 1725, 1248, 1045, 992 cm$^{-1}$.

EXAMPLE 26

(+)-(5RS)-5-Hydroxy-5-[cis-(6RS)-6-((1E,3E)-(5RS)-5-hydroxy-1,3-tridecadienyl)-(1RS)-3-cyclohexen-1-yl]-pentanoic Acid-1,5-lactone Diastereomer B Analogously to example 25, 32 mg of the title compound is obtained as a colorless oil from 67 mg of the acid produced according to example 8.

IR (CHCl$_3$): 3600, 2929, 2860, 1725, 1248, 1045, 992 cm$^{-1}$.

EXAMPLE 27

(+)-(5RS)-5-Hydroxy-5-[cis-(2RS)-2-((1E,3E)-(5RS)-5-hydroxy-1,3-tridecadienyl)-(1RS)-cyclohex-1-yl]-pentanoic Acid-1,5-lactone Diastereomer A Analogously to example 25, 52 mg of the title compound is obtained as a colorless oil from 120 mg of the acid produced according to example 14.

IR (CHCl$_3$): 3620, 2930, 2860, 1725, 1248, 1046, 993 cm$^{-1}$.

EXAMPLE 28

(+)-(5RS)-5-Hydroxy-5-[cis-(2RS)-2-((1E,3E)-(5RS)-5-hydroxy-1,3-tridecadienyl)-(1RS)-cyclohex-1-yl]-pentanoic Acid-1,5-lactone Diastereomer B Analogously to example 25, 41 mg of the title compound is obtained as a colorless oil from 80 mg of the acid produced according to example 17.

IR (CHCl$_3$): 3600, 2930, 2860, 1726, 1248, 1046, 993 cm$^{-1}$.

EXAMPLE 29

(+)-(5RS)-5-Hydroxy-5-[cis-(6RS)-6-((1E,3E)-(5RS)-5-hydroxy-1,3-tridecadienyl)-(1RS)-3-cyclohexen-1-yl]-pentanoic Acid-tris-(hydroxymethyl)-aminomethane Salt A solution of 14 mg of tris-(hydroxymethyl)-aminomethane in 0.04 ml of water is added to a solution of 38 mg of the carboxylic acid, produced according to example 3, in 6 ml of acetonitrile at 70° C. It is allowed to cool with stirring, decanted after 16 hours from the solvent and the residue is dried in a vacuum. 25 mg of the title compound is isolated as a wavy mass.

EXAMPLE 30

(+)-(5RS)-5-Acetoxy-5-[trans(4RS)-6-((1E,3E)-(5RS)-5-acetoxy-1,3-tridecadienyl)-(1RS)-3-cyclohexen-1yl]-pentanol Nonpolar and Polar Diastereomers A solution of 16.7 g of 4-chloro-1-(tert-butyldimethylsilyloxy)-butane in 15 ml of tetrahydrofuran and 0.45 ml of dibromomethane is instilled in 3.65 g of magnesium at 25° C. under argon, heated for 10 minutes to 70° C., stirred for 30 minutes at 25° C. and diluted with 45.2 ml of tetrahydrofuran.

A solution of 1.95 g of trans-(1RS)-1-formyl-(6RS)-6-[(1E,3E)-(5RS)-5-acetoxy-1,3-tridecadienyl]-3-cyclohexene in 5 ml of tetrahydrofuran is instilled in 10 ml of this magnesium organic solution at −20° C. under argon and stirred for 30 minutes at −20° C. It is mixed with 100 ml of saturated ammonium chloride solution, extracted three times with ether, the organic phase is shaken out with brine, dried on magnesium sulfate and concentrated by evaporation in a vacuum. The residue is chromatographed on silica gel. With hexane/ethyl acetate (8+2), 1.85 g of the alcohol is obtained as a colorless oil.

IR (CHCl$_3$): 3600, 2930, 2860, 1725, 1252, 992, 838 cm$^{-1}$.

For acetylation, 5 ml of acetic anhydride is added to a solution of 1.5 g of the above-described alcohol in 30 ml of pyridine and stirred for 16 hours at 24° C. Then, it is concentrated by evaporation with the addition of toluene in a vacuum, and the residue is chromatographed on silica gel. With hexane/ethyl acetate (95+5), 1.64 g of the acetate is obtained as a colorless oil.

IR: 2930, 2860, 1728, 1255, 990, 838 cm$^-$.

For cleavage of protecting groups, 1.2 g of the above-produced acetate is stirred in 85 ml of tetrahydrofuran with 2.0 g of tetrabutylammonium fluoride for 1 hour at 0° C. and for 4 hours at 24° C. under argon. Then, it is diluted with ether, washed three times with water, dried on magnesium sulfate and concentrated by evaporation in a vacuum. The residue is chromatographed with hexane/ethyl acetate (6+4) on silica gel. In this way, 0.45 g of the nonpolar diastereomer is obtained first and then 0.4 g of the polar diastereomer of the title compound as colorless oils.

IR (nonpolar diastereomer): 3600, 3430, 2930, 2858, 1728, 1608, 1375, 1250, 992 cm$^{-1}$.

IR (polar diastereomer): 3620, 3480, 2930, 2860, 1729, 1608, 1375, 1250, 992 cm$^{-1}$.

The initial material for the above-named title compound is produced as follows:

30a) 5-[trans-1-(tert-Butyl-dimethylsilyloxymethyl)-3-cyclohexen-6-yl]-(2E,4E)-pentadienoic acid ethyl ester A solution of 25 g of trans-4-cyclohexene-1,2-dicarboxylic acid diethyl ester in 140 ml of tetrahydrofuran is instilled in a suspension of 10 g of lithium aluminum hydride in 140 ml of tetrahydrofuran at room temperature and the mixture is then stirred for 3 hours at reflux temperature. It is cooled to 0° C., a mixture of tetrahydrofuran/water (1+1) is instilled slowly, stirred for 30 minutes, mixed with 150 ml of chloroform, filtered and the filtrate is concentrated by evaporation in a vacuum. The residue is distilled at 0.2 mm/Hg and at 150° C. in a bulb tube. In this way, 20 g of trans-1,6-dihydroxymethyl-3-cyclohexene is obtained as a colorless oil.

10.6 g of tert-butyldimethylsilyl chloride is added to a solution of 10 g of the above-produced diol and 9.6 g of imidazole in 93 ml of dimethylformamide at 0° C. under argon and stirred for 16 hours at 25° C. It is diluted with 0.6 l of ether, shaken twice with 100 ml of 10% sulfuric acid each, washed neutral with brine, dried on magnesium sulfate and concentrated by evaporation in a vacuum. The residue is chromatographed on silica gel. With hexane/ethyl acetate (9+1), 7.3 g of trans-1-(tert-butyl-dimethylsilyloxymethyl)-6-hydroxymethyl-3-cyclohexene is obtained as a colorless oil.

IR: 3600, 3390, 2930, 2858, 835 cm$^{-1}$.

45 g of Collins reagent (chromic acid-pyridine complex) is added to a solution of 6.6 g of the above-described monosilyl ether in 350 ml of methylene chloride at 0° C. and stirred for 40 minutes at 0° C. Then, it is diluted with a mixture of hexane/ether (3+2), Celite is added, filtered and concentrated by evaporation in a vacuum. The residue is chromatographed with hexane/ethyl acetate (9+1) on silica gel. In this way, 5.5 g of trans-1-(tert-butyl-dimethylsilyloxymethyl)-6-formyl-3-cyclohexene is obtained as a colorless oil.

IR: 2930, 2860, 2730, 1716, 838 cm$^{-1}$.

For Wittig-Horner olefinization, 4.6 g of phosphonocrotonic acid triethyl ester and 2.3 g of diazabicycloundecene (DBU) are added at 24° C. to a stirred suspension of 0.78 g of lithium chloride in 153 ml of acetonitrile and stirred for 10 minutes. Then, a solution of 3.9 g of the above-described aldehyde is instilled in 31 ml of acetonitrile, stirred for 3 hours at 24° C. and then diluted with ether. It is shaken out in succession with water, 10% citric acid solution and water, dried on magnesium sulfate and concentrated by evaporation in a vacuum. The residue is chromatographed with hexane/ethyl acetate (95+5) on silica gel. In this way, 4.1 g of the title compound is obtained as a colorless oil.

IR: 2930, 2858, 1710, 1638, 1618, 1256, 1003, 940, 838 cm$^{-1}$.

30b) 5-[trans-1-(tert-Butyl-dimethylsilyloxymethyl)-3-cyclohexen-6-yl]-(2E,4E)-pentadien-1-al 16.6 ml of a 1.2 molar solution of diisobutyl aluminum hydride in toluene is instilled in a solution of 3.5 g of the ester, produced according to example 30a), in 94 ml of toluene at −70° C. under argon and stirred for 40 minutes at −70° C. Then, 2 ml of isopropanol and then 8 ml of water are instilled, stirred for 2 hours at 22° C., filtered, washed with methylene chloride and concentrated by evaporation in a vacuum. The residue is purified by chromatography on silica gel. With hexane/ethyl acetate (8+2), 3.04 g of the alcohol is obtained as a colorless oil. IR: 3620, 3460, 838 cm$^{-1}$.

A solution of 3.02 g of the above-produced alcohol in 110 ml of toluene is mixed with 8.5 g of manganese dioxide and stirred for 4.5 hours at 24° C. Then, it is filtered, concentrated by evaporation and chromatographed on silica gel. With hexane/ethyl acetate (85+15), 2.9 g of the title compound is eluted as a colorless oil.

IR: 2929, 2860, 1680, 1638, 992, 950, 838 cm$^{-1}$.

30c) (5RS)-5-Acetoxy-1-[trans-1-(tert-butyl-dimethylsilyloxymethyl)-3-cyclohexen-6yl]-(1E,3E)-tridecadiene A solution of 7.95 ml of octyl bromide in 12 ml of ether is instilled in 1.2 g of magnesium in 5 ml of ether with heating and stirred for 30 minutes at 25° C.

A solution of 2.85 g of the aldehyde, produced according to example 30b), in 47 ml of ether is instilled in 5.85 ml (32 10.77 mmol) of this Grignard solution at −20° C. under argon and stirred for 3 hours at −20° C. It is mixed with saturated ammonium chloride solution, extracted three times with ether, the organic phase is shaken out with brine, dried on magnesium sulfate and concentrated by evaporation in a vacuum. The residue is chromatographed on silica gel. With hexane/ethyl acetate (7+3), 2.92 g of the alcohol is eluted as a colorless oil.

IR: 3620, 3460, 2929, 2858, 992, 838.

For acetylation, 5 ml of acetic anhydride is added to a solution of 3.0 g of the above-produced alcohol in 30 ml of pyridine and stirred for 16 hours at 24° C. Then, it is concentrated by evaporation with the addition of toluene in a vacuum, and the residue is chromatographed on silica gel. With hexane/ethyl acetate (8+2), 3.25 g of the title compound is obtained as oil.

IR: 2930, 2858, 1730, 1254, 990, 838 cm$^{-1}$.

30d) trans-(1RS)-1-Formyl-(6RS)-6-[(1E,3E)-(5RS)-5-acetoxy-1,3-tridecadienyl]-3-cyclohexene 6.55 g of tetrabutylammonium fluoride is added to a solution of 3.2 g of the acetate, produced according to example 30c), in 320 ml of tetrahydrofuran at 0° C., stirred for 1 hour at 0° C. and for 3 hours at 24° C. Then, it is diluted with 1.2 l of ether and washed three times with brine. It is dried on magnesium sulfate, concentrated by evaporation in a vacuum and the residue is chromatographed on silica gel. With hexane/ethyl acetate (6+4), 2.34 g of the alcohol is eluted as a colorless oil.

IR: 3620, 3458, 2930, 2860, 1722, 1250, 991 cm$^{-1}$.

18 g of Collins reagent (chromic acid-pyridine complex) is added to a solution of 2.46 g of the above-produced alcohol in 70 ml of methylene chloride at 0° C. and stirred for 15 minutes at 0° C. Then, it is diluted with a mixture of hexane/ether (3+2), Celite is added, filtered and concentrated by evaporation in a vacuum. The aldehyde thus obtained is used without further purification.

EXAMPLE 31

(+)-(5RS)-5-Acetoxy-5-[trans-(6RS)-6-((1E,3E)-(5RS)-5-acetoxy-1,3-tridecadienyl)-(1RS)-cyclohexen-1yl]-pentanoic Acid Diastereomer A 1.98 g of Collins reagent is added to a solution of 360 mg of the nonpolar diastereomeric diacetate, described in example 30, in 28 ml of methylene chloride at 0° C. and stirred for 15 minutes at 0° C. Then, it is diluted with a mixture of hexane/ether (3+2), Celite is added, filtered, washed with hexane/ether (3+2) and concentrated by evaporation in a vacuum.

0.7 ml of Jones reagent (J. Chem. Soc. 1953, 2555) is instilled in a solution of 380 mg of the above-produced aldehyde in 12.5 ml of acetone with stirring at −20° C. and stirred for 12 minutes at −20° C. under argon. Then, 3 ml of isopropanol is added, it is stirred for 10 minutes, diluted with 40 ml of ether, filtered, washed with ether, the ether phase is shaken out twice with brine, dried on magnesium sulfate and concentrated by evaporation in a vacuum. The residue is chromatographed on silica gel. With hexane/ethyl acetate (6+4), 280 mg of the title compound is obtained as a colorless oil.

IR: 3520 (broad), 2928, 2859, 1725, 1372, 1250, 991, 948 cm$^{-1}$.

EXAMPLE 32

(+)-(RS)-5-Hydroxy-5-[trans-(6RS)-6-((1E,3E)-(5RS)-5-hydroxy-1,3-tridecadienyl)-(1RS)-3-cyclohexen-1-yl]-pentanoic Acid Diastereomer A 68 mg of the nonpolar diastereomeric diacetate (diastereomer A) described in example 31 is stirred for 48 hours at 24° C. with 2.5 ml of a solution of potassium hydroxide in water and ethanol (production: 5 g of potassium hydroxide is dissolved in 67.5 ml of water and 182.5 ml of ethanol). Then, it is acidified with 10% citric acid solution to pH 4, extracted four times with 15 ml of methylene chloride each, the organic phase is shaken out with brine, dried on magnesium sulfate and concentrated by evaporation in a vacuum. The residue is chromatographed with ethyl acetate/hexane (8+2) on silica gel. In this way, 41 mg of the title compound is obtained as a colorless oil.

IR: 3620, 3415 (broad), 2929, 2859, 1720, 1375, 992 cm$^{-1}$.

EXAMPLE 33

(+)-(5RS)-5-Acetoxy-5-[trans-(6RS)-6-((1E,3E)-(5RS)-5-hydroxy-1,3-tridecadienyl)-(1RS)-3-cyclohexen-1-yl]-pentanoic Acid Diastereomer A 1.5 ml of a 0.5 normal sodium hydroxide solution is added to a solution of 72 mg of the nonpolar diastereomeric diacetate (diastereomer A), produced according to example 31, in 1.5 ml of methanol at 24° C. and stirred for 7 hours at 24° C. under argon. Then, it is diluted with 2 ml of water and acidified at ice bath temperature with 10% citric acid solution to pH 4. It is extracted four times with 30 ml of ethyl acetate each, the organic phase is shaken out with brine, dried on magnesium sulfate and concentrated by evaporation in a vacuum. The residue is chromatographed on silica gel. With ether/hexane (1+1), 51 mg of the title compound is obtained as a colorless oil.

IR: 3615, 3450, 2930, 2859, 1721, 1375, 1250, 992 cm$^{-1}$.

EXAMPLE 34

(+)-(5RS)-5-Hydroxy-5-[trans-(6RS)-6-((1E,3E)-(5RS)-5-hydroxy-1,3-tridecadienyl)-(1RS)-3-cyclohexen-1-yl]-pentanol Diastereomer A 98 mg of the nonpolar diastereomeric diacetate described in example 30 is stirred for 60 hours at 24° C. with 2.9 ml of a solution of potassium hydroxide in water and ethanol (production: 5 g of potassium hydroxide is dissolved in 67.5 ml of water and 182.5 ml of ethanol). Then, it is acidified with 10% citric acid solution to pH 6, extracted four times with 20 ml of methylene chloride each, the organic phase is shaken out with brine, dried on magnesium sulfate and concentrated by evaporation in a vacuum. The residue is chromatographed with ethyl acetate on silica gel. In this way, 58 mg of the title compound is obtained as a colorless oil.

IR: 3600, 3380 (broad), 2930, 2860, 992 cm$^{-1}$.

EXAMPLE 35

(+)-(5RS)-5-Acetoxy-5-[trans-(6RS)-6-((1E,3E)-(5RS)-5-hydroxy-1,3-tridecadienyl)-(1RS)-3-cyclohexen-1-yl]-pentanol Diastereomer A 60 mg of the nonpolar diastereomeric diacetate, described in example 30, in 1.4 ml of methanol is stirred for 4 hours at 24° C. with 1.4 ml of a 0.5 normal sodium hydroxide solution under argon. Then, it is diluted with 5 ml of water, neutralized with 10% citric acid solution, extracted four times with 20 ml of methylene chloride each, the organic phase is shaken out with brine, dried on magnesium sulfate and concentrated by evaporation in a vacuum. The residue is chromatographed with ethyl acetate/hexane (1+1) on silica gel. In this way, 21 mg of the title compound is obtained as a colorless oil.

IR: 3600, 3450 (broad), 2929, 2860, 1730, 1375, 1252, 993 cm$^{-1}$.

EXAMPLE 36

(+)-(5RS)-5-Acetoxy-5-[trans-(6RS)-6-((1E,3E)-(5RS)-5-acetoxy-1,3-tridecadienyl)-(1RS)-3-cyclohexen-1-yl]-pentanoic Acid Diastereomer B Analogously to example 31, 300 mg of the title compound is obtained as a colorless oil from 405 mg of the polar diastereomeric diacetate produced according to example 30.

IR: 3515 (broad), 2929, 2860, 1725, 1372, 1250, 991, 948 cm$^{-}$.

EXAMPLE 37

(+)-(5RS)-5-Hydroxy-5-[trans-(6RS)-6((1E,3E)-(5RS)-5-hydroxy-1,3-tridecadienyl)-(1RS)-3-cyclohexen-1-yl]-pentanoic Acid Diastereomer B Analogously to example 32, 160 mg of the title compound is obtained as a colorless oil from 220 mg of the diacetate (diastereomer B) produced according to example 36.

IR: 3600, 3420 (broad), 2930, 2860, 1721, 1375, 992 cm$^{-1}$.

EXAMPLE 38

(+)-(5RS)-5-Acetoxy-5-[trans-(6RS)-6-((1E,3E)-(5RS)-5-hydroxy-1,3-tridecadienyl)-(1RS)-3-cyclohexen-1-yl]-pentanoic Acid Diastereomer B Analogously to example 33, 60 mg of the title compound is obtained as a colorless oil from 120 mg of the diacetate (diastereomer B) produced according to example 36.

IR: 3620, 3400 (broad), 2930, 2860, 1722, 1375, 1250, 992 cm$^{-1}$.

EXAMPLE 39

(+)-(5RS)-5-Hydroxy-5-[trans-(6RS)-6-((1E,3E)-(5RS)-5-hydroxy-1,3-tridecadienyl)-(1RS)-3-cyclohex-en-1-yl]-pentanol Diastereomer B Analogously to example 34, 72 mg of the title compound is obtained as a colorless oil from 140 mg of the polar diastereomeric diacetate produced in example 30.

IR: 3600, 3420 (broad), 2930, 2860, 992 cm$^{-1}$.

EXAMPLE 40

(+)-(5RS)-5-Acetoxy-5-[trans-(6RS)-6-((1E,3E)-(5RS)-5-hydroxy-1,3-tridecadienyl)-(1RS)-3-cyclohexen-1-yl]-pentanol Diastereomer B Analogously to example 35, 30 mg of the title compound is obtained as a colorless oil from 50 mg of the polar diastereomeric diacetate produced in example 30.

IR: 3620, 3430 (broad), 2930, 2860, 1729, 1376, 1250, 993 cm$^{-1}$.

EXAMPLE 41

(+)-(5RS)-5-Acetoxy-5-[trans-(2RS)-2-((1E,3E)-(5RS)-5-acetoxy-1,3-tridecadienyl)-(1RS)-cyclohex-1-yl]-pentanol Nonpolar and Polar Diastereomer Analogously to example 30, 0.5 g of nonpolar diastereomer and 0.6 g of polar diastereomer of the title compound are obtained as colorless oils from 2 g of trans-(1RS)-1-formyl-(2RS)-2-[(1E,3E)-(5RS)-5-acetoxy-1,3-tridecadienyl)-cyclohexane.

IR (nonpolar diastereomer): 3620, 3420, 2929, 2859, 1729, 1607, 1375, 1250, 992 cm$^{-}$.

IR (polar diastereomer): 3600, 3430, 2929, 2860, 1729, 1607, 1375, 1250, 992 cm$^{-1}$.

The initial material for the above-named title compound is produced as follows:

41a) 5-[trans-1-(tert-Butyl-dimethylsilyloxymethyl)-cyclohex-2-yl]-(2E,4E)-pentadienoic acid ethyl ester Analogously to example 30a, the title compound is obtained as a colorless oil from trans-1,2-dihydroxymethylcyclohexane.

IR: 2930, 2859, 1710, 1638, 1618, 1255, 1004, 940, 838 cm$^{-1}$.

41b) 5-[trans-1-(tert-Butyl-dimethylsilyloxymethyl)-cyclohex-2-yl]-(2E,4E)-pentadien-1-al Analogously to example 30b), 28 g of the title compound is obtained as a colorless oil from 33 g of the ester produced according to example 41a).

IR: 2930, 2859, 1680, 1640, 993, 950, 840 cm$^{-1}$.

41c) (5RS)-5Acetoxy-1-[trans-1-(tert-butyl-dimethyl-silyloxymethyl)-cyclohex-1-yl]-(1E,3E)-tridecadiene Analogously to example 30c), 7.5 g of the title compound is obtained as a colorless oil from 8.3 g of the aldehyde produced according to example 42b).

IR: 2930, 2860, 1731, 1255, 993, 838 cm$^{-1}$.

41d) trans-(1RS)-1-Formyl-(2RS)2-[(1E,3E)-(5RS)-5-acetoxy-1,3-tridecadienyl]-cyclohexane Analogously to example 30d), 3.0 g of the aldehyde is obtained as crude product from 4.3 g of the acetate produced according to example 30c).

EXAMPLE 42

(+)-(5RS)-5-Acetoxy-5-[trans-(2RS)-2-((1E,3E)-(5RS)-5-acetoxy-1,3-tridecadienyl)-(1RS)-cyclohex-1-yl]-pentanoic Acid Diastereomer A Analogously to example 31, 390 mg of the title compound is obtained as a colorless oil from 500 mg of the nonpolar diastereomeric diacetate produced according to example 41.

IR: 3500 (broad), 2930, 2860, 1725, 1373, 1251, 991, 948 cm$^{-1}$.

EXAMPLE 43

(+)-(5RS)-5-Hydroxy-5-[trans-(2RS)-2-((1E,3E)-(5RS)5-hydroxy-1,3-tridecadienyl)-(1RS)-cyclohex-1-yl]-pentanoic Acid diastereomer A Analogously to example 32, 203 mg of the title compound is obtained as a colorless oil from 300 mg of the diacetate (diastereomer A) produced according to example 42.

IR: 3620, 3410 (broad), 2930, 2859, 1720, 1375, 993 cm$^{-1}$.

EXAMPLE 44

(+)-(5RS)-5-Acetoxy-5-[trans-(2RS)-2-((1E,3E)-(5RS)-5-hydroxy-1,3-tridecadienyl)-(1RS)-cyclohex-1-yl]-pentanoic Acid Diastereomer A Analogously to example 33, 70 mg of the title compound is obtained as a colorless oil from 120 mg of the diacetate (diastereomer A) produced according to example 42.

IR: 3620, 3430, 2929, 2859, 1722, 1375, 1250, 992 cm$^{-1}$.

EXAMPLE 45

(+)-(5RS)-5-Acetoxy-5-[trans-(2RS)-2-((1E,3E)-(5RS)-5-acetoxy-1,3-tridecadienyl)-(1RS)-cyclohex-1-yl]-pentanoic Acid Diastereomer B Analogously to example 31, 180 mg of the title compound is obtained as a colorless oil from 290 mg of the polar diastereomeric diacetate produced according to example 41.

IR: 3620 (broad), 2930, 2860, 1725, 1375, 1250, 991, 948 cm$^{-1}$.

EXAMPLE 46

(+)-(5RS)-5-Hydroxy-5-[trans-(2RS)-2-((1E,3E)-(5RS)-5-hydroxy-1,3-tridecadienyl)-(1RS)-cyclohex-1-yl]-pentanoic Acid Diastereomer B Analogously to example 32, 205 mg of the title compound is obtained as a colorless oil from 310 mg of the diacetate (diastereomer B) produced according to example 45.

IR: 3620, 3415 (broad), 2930, 2860, 1720, 1375, 993 cm$^{-1}$.

EXAMPLE 47

(+)-(5RS)-5-Acetoxy-5-[trans-(2RS)-2-((1E,3E)-(5RS)-5-hydroxy-1,3-tridecadienyl)-(1RS)-cyclohex-1yl]-pentanoic Acid Diastereomer B Analogously to example 33, 70 mg of the title compound is obtained as a colorless oil from 150 mg of the diacetate (diastereomer B) produced according to example 45.

IR: 3600, 3410, 2930, 2860, 1722, 1376, 1251, 992 cm$^{-1}$.

EXAMPLE 48

(+)-(5RS)-5-Acetoxy-5-[trans-(6RS)-6-((1E,3E)-(5RS)-5-acetoxy-1,3-tridecadienyl)-(1RS)-3-cyclohexen-1-yl]-pentanoic Acid Methyl Ester Diastereomer A An ethereal diazomethane solution is instilled until permanent yellow coloring in a solution of 150 mg of the acid, produced according to example 31, in 15 ml of methylene chloride at 0° C. and stirred for 15 minutes at 0° C. Then, it is concentrated by evaporation in a vacuum, and the residue is chromatographed on silica gel. With hexane/ethyl acetate (9+1), 140 mg of the title compound is obtained as a colorless oil.

IR (film): 2923, 2851, 1739, 1655, 1370, 1240, 990 cm$^{-1}$.

EXAMPLE 49

(+)-(5RS)-5-Hydroxy-5-[trans-(6RS)-6-((1E,3E)-(5RS)-5-hydroxy-1,3-tridecadienyl)-(1RS)-3-cyclohexen-1-yl]-pentanoic Acid Methyl Ester Diastereomer A An ethereal diazomethane solution is instilled until permanent yellow coloring in a solution of 80 mg of the acid, produced according to example 32, in 8 ml of methylene chloride at 0° C. and stirred for 15 minutes at 0° C. Then, it is concentrated by evaporation in a vacuum, and the residue is chromatographed on silica gel. With hexane/ethyl acetate (1+9), 70 mg of the title compound is obtained as a colorless oil.

IR (film): 3620, 2922, 2853, 1738, 1655, 1435, 990 cm$^{-1}$.

EXAMPLE 50

(+)-(5RS)-5-Acetoxy-5-[trans-(6RS)-6-((1E,3E)-(5RS)-5-hydroxy-1,3-tridecadienyl)-(1RS)-3-cyclohexen-1-yl]-pentanoic Acid Methyl Ester Diastereomer A An ethereal diazomethane solution is instilled until permanent yellow coloring in a solution of 48 mg of the acid, produced according to example 33, in 5 ml of methylene chloride at 0° C. and stirred for 15 minutes at 0° c. Then, it is concentrated by evaporation in a vacuum, and the residue is chromatographed on silica gel. With hexane/ethyl acetate (1+1), 38 mg of the title compound is obtained as a colorless oil.

IR (film): 3400, 2923, 2858, 1740, 1655, 1370, 1240, 990 cm$^{-1}$.

EXAMPLE 51

(+)-(5RS)-5-Acetoxy-5-[trans-(2RS)-2-((1E,3E)-(5RS)-5-acetoxy-1,3-tridecadienyl)-(1RS)-cyclohex-1-yl]-pentanoic Acid Methyl Ester Diastereomer A Analogously to example 48, 51 mg of the title compound is obtained as a colorless oil from 67 mg of the acid produced according to example 42.

IR (film): 2924, 2852, 1740, 1655, 1371, 1240, 991 cm$^{-1}$.

EXAMPLE 52

(+)-(5RS)-5-Hydroxy-5-[trans-(2RS)-2-((1E,3E)-(5RS)-5-hydroxy-1,3-tridecadienyl)-(1RS)-cyclohex-1-yl]-pentanoic Aid Methyl Ester Diastereomer A Analogously to example 49, 22 mg of the title compound is obtained as a colorless oil from 29 mg of the acid produced according to example 43.

IR (film): 3600, 2922, 2852, 1738, 1655, 1436, 991 cm$^{-1}$.

EXAMPLE 53

(+)-(5RS)-5-Acetoxy-5-[trans-(2RS)-2-((1E,3E)-(5RS)-5-hydroxy-1,3-tridecadienyl)-(1RS)-cyclohex-1-yl]-pentanoic Acid Methyl Ester Diastereomer A Analogously to example 50, 57 mg of the title compound is obtained as a colorless oil from 65 mg of the acid produced according to example 44.

IR (film): 3420, 2924, 2859, 1740, 1655, 1370, 1240, 990 cm$^{-1}$.

EXAMPLE 54

(+)-(5RS)-5-Hydroxy-5-[trans-(6RS)-6-((1E,3E)-(5RS)-5-hydroxy-1,3-tridecadienyl)-(1RS)-3-cyclohexen-1-yl]-pentanoic Acid-1,5-lactone Diastereomer A 1 g of anhydrous magnesium sulfate is added in ports to a solution of 50 mg of the acid, produced according to example 32, in 10 ml of toluene at 24° C. over a period of 24 hours and stirred for another 24 hours at 24° C. Then it is filtered and the evaporation residue is chromatographed on silica gel. With toluene/ethyl acetate (7+3), 28 mg of the lactone is eluted as a colorless oil.

IR (CHCl$_3$): 3620, 2930, 2860, 1726, 1248, 1045, 992 cm$^{-1}$.

EXAMPLE 55

(+)-(5RS)-5-Hydroxy-5-[trans-(6RS)-6-((1E,3E)-(5RS)-5-hydroxy-1,3-tridecadienyl)-(1RS)-3-cyclohexen-1-yl]-pentanoic Acid-1,5-lactone Diastereomer B Analogously to example 54, 30 mg of the title compound is obtained as a colorless oil from 60 mg of the acid produced according to example 37.

IR (CHCl$_3$): 3620, 2930, 2860, 1725, 1248, 1045, 992 cm$^{-1}$.

EXAMPLE 56

(+)-(5RS)-5-Hydroxy-5-[trans-(2RS)-((1E,3E)-(5RS)-5-hydroxy-1,3-tridecadienyl)-(1RS)-cyclohex-1-yl]-pentanoic Acid-1,5-lactone Diastereomer A Analogously to example 54, 40 mg of the title compound is obtained as a colorless oil from 100 mg of the acid produced according to example 43.

IR (CHCl$_3$): 3600, 2930, 2860, 1726, 1248, 1046, 993 cm$^{-1}$.

EXAMPLE 57

(+)-(5RS)-5-Hydroxy-5-[trans-(2RS)-2-((1E,3E)-(5RS)-5-hydroxy-1,3-tridecadienyl)-(1RS)-cyclohex-1-yl]-pentanoic Acid-1,5-lactone Diastereomer B Analogously to example 54, 23 mg of the title compound is obtained as a colorless oil from 40 mg of the acid produced according to example 46.

IR (CHCl$_3$): 3620, 2930, 2860, 1725, 1248, 1046, 993 cm$^{-1}$.

EXAMPLE 58

(+)-(5RS)-5-Hydroxy-5-[trans-(6RS)-6-((1E,3E)-(5RS)-5-hydroxy-1,3-tridecadienyl)-(1RS)-3-cyclohexen-1-yl]-pentanoic Acid-tris-(hydroxymethyl)-aminomethane Salt A solution of 29 mg of tris-(hydroxymethyl)-aminomethane in 0.04 ml of water is added to a solution of 80 mg of the carboxylic acid, produced according to example 23, in 13 ml of acetonitrile at 70° C. It is allowed to cool with stirring, decanted after 16 hours from the solvent and the residue is dried in a vacuum. 25 mg of the title compound is isolated as a waxy mass.

EXAMPLE 59

(±)-(5RS)-5-Acetoxy-5-[cis-(2RS)-2-((1E,3E)-(5RS)-5-hydroxy-trideca-1,3-dien-7-inyl)-(1RS)-cyclohex-1-yl]-pentanoic Acid Nonpolar and Polar Diastereomer A solution of 2.22 g of 4-chloro-1-(tert-butyldimethylsilyloxy)-butane in 2 ml of tetrahydrofuran and 0.06 ml of dibromoethane is instilled in 480 mg of magnesium at 25° C. under argon, hated for 10 minutes to 60° C., stirred for 30 minutes at 25° C. and diluted with 6.2 ml of tetrahydrofuran.

4 ml of the above-produced Grignard solution is added to 922 mg of cis-(1RS)-1-formyl-(2RS)-[(1E,3E)-(5RS)-5-tert-butyldiphenylsilyloxy-trideca-1,3-dien-7-inyl]-cyclohexane dissolved in 5 ml of tetrahydrofuran at −70° C. under argon and stirred for 1 hour at −70° C. The reaction mixture is added to the saturated ammonium chloride solution, extracted several times with ether, the organic phase is washed with brine, dried on sodium sulfate and concentrated by evaporation in a vacuum. The residue thus obtained is dissolved in 4 ml of pyridine, 1 ml of acetic anhydride under argon is added and stirred for 24 hours at 24° C. Then, it is concentrated by evaporation with the addition of toluene in a vacuum. The residue is chromatographed on silica gel with hexane/0–50% of methylene chloride. 487 mg of (±)-(5RS)- 5-acetoxy-5-[cis-(2RS)-2-((1E,3E)-(5RS)-5-tert-butyldiphenylsilyloxy-trideca-1,3-dien-7inyl)-(1RS)-cyclohex-1-yl]-pentan-1-ol-tert-butyldimethyl-silylether is obtained as a colorless oil.

IR: 2935, 2860, 1730, 1255, 1122, 992, 843, 705 cm$^{-1}$.

For selective cleavage of protecting groups, 400 mg of the above-produced acetate in 5 ml of ethanol is stirred with 400 mg of pyridinium-p-toluene-sulfonate for 1 hour at 60° C. under argon. After cooling off to 24° C., it is diluted with ether, washed twice with water, dried on sodium sulfate and concentrated by evaporation in a vacuum. The residue is chromatographed on silica gel with hexane/0–40% ethyl acetate. 227 mg of (±)-(5RS)-5-acetoxy-5-[cis-(2RS)-2-((1E,3E)-(5RS)-5-tert-butyldiphenylsilyloxy-trideca-1,3-dien-7-inyl)-(1RS)-cyclohex-1-yl]-pentan-1-ol is thus obtained as a colorless oil.

IR: 3680, 3440, 2935, 2860, 1730, 1255, 1122, 990, 705 cm$^{-1}$.

220 mg of the above-produced alcohol in 22 ml of methylene chloride is mixed at 0° C. under argon with 1.76 g of Collins reagent (chromic acid-pyridine complex) and stirred for 30 minutes at 0° C. It is diluted with hexane/ether (1+1), filtered off on Celite, subsequently washed with hexane/ether (1+1) and concentrated by evaporation in a vacuum.

1.0 ml of Jones reagent (J. Chem. Soc. 1953, 2555) is instilled in a solution of 237 mg of the above-produced aldehyde in 10 ml of acetone with stirring at −30° C. and stirred for 30 minutes at −20° C. under argon. Then, 0.3 ml of isopropanol is added, stirred for 10 minutes at −20° C., diluted with ether, washed neutral with brine/water (1+1), dried on sodium sulfate and concentrated by evaporation in a vacuum. The residue is chromatographed on silica gel with hexane/ethyl acetate (7+3). 171 mg of (±)-(5RS)-5-acetoxy-5-[cis-(2RS)-2-((1E,3E)-(5RS)-5-tert-butyldiphenylsilyloxy-trideca-1,3-dien-7-inyl)-(1RS)-cyclohex-1-yl]-pentanoic acid is thus obtained as a colorless oil.

IR: 3520, 3200, 2935, 2860, 1725, 1255, 1120, 990, 703 cm$^{-1}$.

20 mg of the above-produced acid dissolved in 1 ml of tetrahydrofuran is mixed with 100 mg of tetrabutylammonium fluoride and stirred over 16 hours at 24° C. under argon. Then, it is diluted with ether, washed with brine, dried on sodium sulfate and concentrated by evaporation in a vacuum. The residue is chromatographed on silica gel with hexane/30–60% of ethyl acetate. In this way, first 4.7 mg of the nonpolar diastereomer and then 5.5 mg of the polar diastereomer of the title compound are obtained as colorless oils.

IR (nonpolar diastereomer): 3590, 3410, 2930, 2860, 1725, 1250, 1120, 991 cm$^{-1}$.

IR (polar diastereomer): 3600, 3400, 2928, 2859, 1730, 1250, 1122, 990 cm$^{-1}$.

The initial material for the above-named title compound is produced as follows:

a) 1-[cis-(2RS)-2-(tert-Butyldimethylsilyloxymethyl)-(1RS)-cyclohex-1-yl]-(1E,3E)-(5RS)-octa-1,3-dien-7-in-5-ol Several crystals of iodine and 12.5 mg of mercury(II) chloride are added to 2.05 g of magnesium in 25 ml of ether. Altogether, 7.5 ml of propargyl bromide is instilled in the pure bromide at 24° C. until the Grignard reaction is started. Then, the residual bromide dissolved in 25 ml of ether is slowly instilled at 0° C. and subsequently stirred after the complete addition for 1 more hour at 24° C.

63 mg of mercury(II) chloride is added to a solution of 8.1 g of 5-[cis-1-(tert-butyldimethylsilyloxymethyl)-cyclohex-2-yl]-(2E,4E)-pentadien-1-al (produced according to example 12b) in 125 ml of ether and 40 ml of the above-produced Grignard solution is instilled slowly at −70° C. under argon. Then, it is allowed to heat to 0° C. and is stirred at this temperature for another 30 minutes. The reaction mixture is then added to saturated ammonium chloride solution and extracted several times with ether. The organic phase is washed with brine, dried on sodium sulfate and concentrated by evaporation in a vacuum. The residue is chromatographed on silica gel with hexane/0–40% of ethyl acetate. 7.48 g of the title compound is thus obtained as a colorless oil.

IR: 3390, 3315, 2930, 2860, 2120, 990, 838 cm$^{-1}$.

b) 1-[cis-(2RS)-2-(tert-Butyldimethylsilyloxymethyl)-(1RS)-cyclohex-1-yl]-(1E,3E)-(5RS)-octa-1,3-dien-7-in-5-ol-tert-butyldiphenylsilylether 7.48 g of the above-produced alcohol dissolved in 130 ml of dimethylformamide is mixed with 4.64 g of imidazole. 7.97 g of tert-butyl-diphenylsilyl chloride is added to this solution at 0° under argon and stirred for 16 hours at 24° C. Then, the reaction mixture is added to water, extracted several times with hexane/ether (1+1), dried on sodium sulfate and concentrated by evaporation in a vacuum. The residue is chromatographed on silica gel with hexane/0–30% of ether. 11.7 g of the title compound is thus obtained as a colorless oil.

IR: 3320, 2925, 2862, 2125, 1120, 992, 840, 705 cm$^{-1}$.

c) 1-[cis-(2RS)-2-(tert-Butyldimethylsilyloxymethyl)-(1RS)-cyclohex-1-yl]-(1E,3E)-(5RS)-trideca-1,3-dien-7-in-5-ol-tert-butyldiphenylsilylether 11.7 g of the above-produced silyl ether in 100 ml of tetrahydrofuran is mixed at −70° C. under argon with 19 ml of a 1.6 molar n-butyllithium solution in hexane. It is allowed to heat to −10° C. and is stirred at this temperature for 30 minutes. Then, 10 ml of a n-pentyl bromide, 16 ml of hexamethylphosphoric acid triamide and 400 mg of sodium iodide are added in succession and stirred for 6 hours at 24° C. The reaction mixture is added to water, extracted several times with ether, dried on sodium sulfate and concentrated by evaporation in a vacuum. The residue is chromatographed on silica gel with hexane/methylene chloride (8+2). 7.6 g of the title compound is thus obtained as a colorless oil.

IR: 2928, 2860, 1122, 990, 838, 700 cm$^{-1}$.

d) cis-(1RS)-1-Hydroxymethyl-(2RS)-[(1E,3E)-(5RS)-5-tert-butyldiphenylsilyloxy-trideca-1,3-dien-7-in]-cyclohexane 100 ml of a mixture of acetic acid/water/THF (65:35:10) is added to 7.6 g of the above-produced silyl ether dissolved in 100 ml of tetrahydrofuran and stirred for 10 hours to 50° C. It is concentrated by evaporation in a vacuum with the addition of toluene. The residue is chromatographed on silica gel with hexane/0–40% of ethyl acetate. 5.7 g of the title compound is thus obtained as a colorless oil.

IR: 3580, 3350, 3315, 2930, 2860, 1122, 990, 702 cm$^{-1}$.

e) cis-(1RS)-1-Formyl-(2RS)-[(1E,3E)-(5RS)-5-tert-butyldiphenylsilyloxy-trideca-1,3-dien-7-in]-cyclohexane 1.0 g of the above-produced alcohol in 80 ml of methylene chloride is mixed at 0° C. under argon with 6 g of Collins reagent (chromic acid-pyridine complex) and stirred for 30 minutes at 0° C. Then, it is filtered off on Celite, subsequently washed with ether and concentrated by evaporation in a vacuum. The aldehyde thus obtained is used without further purification.

EXAMPLE 60

90 mg of (±)-(5RS)-5-acetoxy-5-[cis-(2RS)-2-((1E,3E)-(5RS)-5-tert-butyldiphenylsilyloxy-trideca-1,3-dien-7-inyl)-(1RS)-cyclohex-1-yl]-pentanoic acid (produced in example 59) is stirred together with 1.8 ml of ethanolic potassium hydroxide solution (5 g of potassium hydroxide in 62.5 ml of water and 187.5 ml of ethanol) for 4 days at 24° C. Then, it is acidified with 10% sulfuric acid to pH 5, extracted several times with ethyl acetate, the organic phase is washed with brine, dried on sodium sulfate and concentrated by evaporation in a vacuum. The residue is chromatographed on silica gel with hexane/10–70% of ethyl acetate. 32 mg of (±)-(5RS)-5-acetoxy-5-[cis-(2RS)-2-((1E,3E)-(5RS)-5-hydroxy-trideca-1,3-dien-7-inyl)-(1RS)-cyclohex-1-yl]-pentanoic acid is obtained.

IR: 3600, 3420, 2928, 2860, 1725, 1250, 1122, 990, 705 cm$^{-1}$.

32 mg of the above-produced alcohol dissolved in 1.5 ml of tetrahydrofuran is mixed at 24° C. under argon with 180 mg of tetrabutylammonium fluoride and stirred for 16 hours at this temperature. Then, it is diluted with ether, the organic phase is washed with brine, dried on sodium sulfate and concentrated by evaporation in a vacuum. The residue is chromatographed on silica gel with hexane/30–70% of ethyl acetate. 6.5 mg of the title compound is obtained as a colorless oil.

IR: 3600, 3410, 2930, 2862, 1728, 1250, 1120, 990 cm$^{-1}$.

EXAMPLE 61

(±)-(5RS)-5-Acetoxy-5-[cis-(2RS)-2-((1E,3E,7Z)-(5RS)-5-hydroxy-1,3,7-tridecatrienyl)-(1RS)-cyclohex-1-yl]-pentanoic Acid Diastereomers A and B A solution of 4.44 g of 4-chloro-1-(tert-butyldimethylsilyloxy)-butane in 4 ml of tetrahydrofuran and 0.06 ml of dibromomethane is instilled in 960 mg of magnesium at 25° C. under argon, heated for 10 minutes to 60° C., stirred for 30 minutes at 25° C. and diluted with 12.4 ml of tetrahydrofuran. 9 ml of the above-produced Grignard solution is added to 1.95 g of cis-(1RS)-1-formyl-(2RS)-[(1E,3E,7Z)-(5RS)-5-tert-butyldiphenylsilyloxy-1,3,7-tridecatrienyl]-cyclohexane dissolved in 10 ml of tetrahydrofuran at −70° C. under argon and stirred for 1 hour at −70° C. The reaction mixture is added to saturated ammonium chloride solution, extracted several times with ether, the organic phase is washed with brine, dried on sodium sulfate and concentrated by evaporation in a vacuum. The residue thus obtained is dissolved in 8 ml of pyridine, 2 ml of acetic anhydride under argon is added and stirred for 20 hours at 24° C. Then, it is concentrated by evaporation in a vacuum with the addition of toluene. The residue is chromatographed on silica gel with hexane/ether (98+2). 602 mg of a nonpolar diastereomer and 621 mg of a polar diastereomer are obtained as colorless oils from (±)-(5RS)-5-acetoxy-5-[cis-(2RS)-2-((1E,3E,7Z)-(5RS)-5-tert-butyldiphenylsilyloxy-1,3,7-tridecatrienyl)-(1RS)-cyclohex-1-yl]-pentan- 1-ol-tert-butyldimethylsilylether.

IR (nonpolar diastereomer): 2928, 2858, 1738, 1245, 988, 837, 703 cm$^{-1}$.

IR (polar diastereomer): 2928, 2857, 1738, 1243, 990, 835, 702 cm$^{-1}$.

2.4 ml of an HF-pyridine solution (1 ml of HF-pyridine complex+3 ml of pyrinde+3 ml of tetrahydrofuran) is added to a solution of 240 mg of the above-produced nonpolar acetate in 12 ml of methanol at 24° C. under argon and stirred for 6 hours at 24° c. It is diluted with ether, the organic phase is washed with saturated sodium bicarbonate solution, with brine, dried on sodium sulfate, filtered and concentrated by evaporation in a vacuum. The residue is chromatographed on silica gel with hexane/0-50% of ethyl acetate. 97 mg of (±)-(5RS)-5-acetoxy-5-[cis-(2RS)-2-((1E,3E,7Z)-(5RS)-5-tert-butyldiphenylsilyloxy-1,3,7-tridecatrienyl)-(1RS)-cyclohex-1-yl]-pentan-1-ol (diastereomer A) is obtained as a colorless oil.

IR (diastereomer A): 3450, 2930, 2860, 1735, 1242, 988, 702 cm$^{-1}$.

Analogously to the above-described method, 169 mg of diastereomer B is obtained from 621 mg of the above--produced polar acetate.

IR (diastereomer B); 3440, 2929, 2858, 1738, 1242, 990, 702 cm$^{-1}$.

97 mg of the above-produced alcohol (diastereomer A) in 5 ml of methylene chloride is mixed at 0° C. under argon with 400 mg of Collins reagent (chromic acid-pyridine complex) and stirred for 30 minutes at 0° C. It is diluted with hexane/ether (1+1), filtered off on Celite, subsequently washed with hexane/ether (1+1) and concentrated by evaporation in a vacuum. The residue thus obtained is dissolved in 4 ml of acetone, 94 mg of Jones reagent (J. Chem. Soc. 1953, 2555) is instilled with stirring at −20° C. and stirred for 25 minutes at −20° C. under argon. Then, 0.1 ml of isopropanol is added, stirred for 10 minutes at −20° C., diluted with ether, washed neutral with brine/water (1+1), dried on sodium sulfate and concentrated by evaporation in a vacuum. The residue is chromatographed on silica gel with hexane/0-30% of ethyl acetate. 65 mg of (±)-(5RS)-5-acetoxy-5-[cis-(2RS)-2-((1E,3E,7Z)-(5RS)-5-tert-butyldiphenylsilyloxy-1,3,7-tridecatrienyl)-(1RS)-cyclohex-1-yl]-pentanoic acid (diastereomer A) is obtained as a colorless oil.

IR (diastereomer A): 3440, 3200, 2929, 2858, 1735, 1710, 1240, 990, 702 cm$^{-1}$.

Analogously to the above-described methodology, 162 mg of acid (diastereomer B) is obtained as a colorless oil from 261 mg of the above-produced alcohol (diastereomer A).

IR (diastereomer B): 3450, 3200, 2930, 2858, 1738, 1708, 1240, 988, 702 cm$^{-1}$.

65 mg of the above-produced acid (diastereomer A) dissolved in 2.7 ml of tetrahydrofuran is mixed with 366 mg of tetrabutylammonium fluoride and stirred for 16 hours at 24° C. under argon. Then, it is diluted with ether, washed with brine, dried on sodium sulfate and concentrated by evaporation in a vacuum. The residue is chromatographed on silica gel with hexane/50-70% of ethyl acetate. 24 mg of the title compound (diastereomer A) is obtained as a colorless oil.

IR (diastereomer A): 3450, 3200, 2930, 2858, 1735, 1710, 1240, 988, 702 cm$^{-1}$.

Analogously to the above-described methodology, 64 mg of the title compound (diastereomer B) is obtained as a colorless oil from 160 mg of the above-produced acid (diastereomer B).

IR (diastereomer B): 3440, 2928, 2857, 1710, 1242, 990 cm$^{-1}$.

The initial material for the above-named title compound is produced as follows:

a) cis-(1RS)-1-Hydroxymethyl-(2RS)-[(1E,3E,7Z)-(5RS)-5-tert-butyldiphenylsilyloxy-1,3,7-tridecatrienyl]-cyclohexane For hydrogenation, 6.2 g of cis-(1RS)-1-hydroxymethyl-(2RS)-[(1E,3)-(5RS)-5-tert-butyldiphenylsilyloxy-trideca-1,3-dien-7-in]-cyclohexane in 2.5 l of hexane/ethyl acetate (1+1) is stirred with 6.2 g of Lindlar catalyst for 3 hours at 24° C. in a hydrogen atmosphere. Then, it is flushed with nitrogen, filtered and concentrated by evaporation in a vacuum. The residue is chromatographed on silica gel with hexane/tert-butyl methyl ether (9+1). 3.43 g of the title compound is obtained as a colorless oil.

IR: 3590, 3340, 2925, 2855, 988, 698 cm$^{-1}$.

b) cis-(1RS)-1-Formyl-(2RS)[(1E,3E,7Z)-(5RS)-5-tert-butyldiphenylsilyloxy-1,3,7-tridecatrienyl]-cyclohexane Analogously to example 59e, 1.9 g of the title compound is obtained as a colorless oil from 2.0 g of the above-produced alcohol.

IR: 2930, 2858, 2720, 1718, 990, 700 cm$^{-1}$.

EXAMPLE 62

(±)-(5RS)-5-Hydroxy-5-[cis-(2RS)-2-((1E,3E,7Z)-(5RS)-5-hydroxy-1,3,7-tridecatrienyl)-(1RS)-cyclohex-1-yl]-pentanoic Acid Diastereomer A 20 mg of (±)-(5RS)-5-acetoxy-5-[cis-(2RS)-2-((1E,3E,7Z)-(5RS)-5-hydroxy-1,3,7-tridecatrienyl)-(1RS)-cyclohex-1yl]-pentanoic acid (diastereomer A, produced in example 61) dissolved in 0.6 ml of methanol is mixed with 0.6 ml of 0.5N lithium hydroxide solution and stirred for 24 hours at 50° C. under argon. Then, it is diluted with 1 ml of water and acidified at 0° C .with a 1N sulfuric acid to pH 5. It is extracted several times with water, the organic phase is washed with brine, dried on sodium sulfate and concentrated by evaporation in a vacuum. The residue is chromatographed on silica gel with hexane/50-90% of ethyl acetate. 11.2 mg of the title compound is obtained as a colorless oil.

IR: 3445, 2932, 2860, 1708, 1240, 990 cm$^{-1}$.

EXAMPLE 63

(±)-(5RS)-5-Hydroxy-5-[cis-(2RS)-2-((1E,3E,7Z)-(5RS)-5-hydroxy-1,3,7-tridecatrienyl)-(1RS)-cyclohex-1-yl]-pentanoic Acid (Diastereomer B)

Analogously to example 62, 19 mg of the title compound is obtained as a colorless oil from 48 mg of the acid (diastereomer B) produced according to example 61.

IR: 3440, 2930, 2858, 1710, 1240, 990 cm$^{-1}$.

EXAMPLE 64

(±)-(5RS)-5-Acetoxy-5-[cis-(2RS)-2-((1E,3E)-(5RS)-5-acetoxy-6-(2-pentylphenyl)-1,3-hexadienyl)-(1RS)-cyclohex-1-yl]-pentan-1-ol Diastereomer A A solution of 2.2 g of 4-chloro-1-(tert-butyldimethylsilyloxy)-butane in 2 ml of tetrahydrofuran and 0.06 ml of dibromoethane is instilled in 480 mg of magnesium at 25° C. under argon, heated for 10 minutes to 60° C., stirred for 30 minutes at 25° C. and diluted with 6.2 ml of tetrahydrofuran.

3 ml of the above-produced Grignard solution is added to 670 mg of cis-(1RS)-1-formyl-(2RS)-[(1E,3E)-(5RS)-5-acetoxy-6-(2-pentylphenyl)-1,3-hexadienyl]-cyclohexane (diastereomer A) in 5 ml of tetrahydrofuran at −70° C. under argon and stirred for 1 hour at −70° C. The reaction mixture is added to saturated ammonium chloride solution, extracted several times with ether, the organic phase is washed with brine, dried on sodium sulfate and concentrated by evaporation in a vacuum. The residue thus obtained is dissolved in 8 ml of pyridine, 2 ml of acetic anhydride is added under argon and stirred for 24 hours at 24° C. Then, it is concentrated by evaporation in a vacuum with the addition of toluene. The residue is chromatographed on silica gel with hexane/0–10% of ethyl acetate. 304 mg of (±)-(5RS)-5-acetoxy-5-[cis-(2RS)-2-((1E,3E)-(5RS)-5-acetoxy-6-(2-pentylphenyl)-1,3-hexadienyl)-(1RS)-cyclohex-1-yl]-pentan-1-ol-tert-butyldimethylsilylether (diastereomer A) is obtained.

IR: 2940, 2870, 1728, 1610, 1255 972, 842 cm$^{-1}$.

For cleavage of protecting groups, 290 mg of the above-produced acetate dissolved in 29 ml of tetrahydrofuran is mixed with 438 mg of tetrabutylammonium fluoride and stirred for 4 hours at 24° C. under argon. Then, it is diluted with ether, the organic phase is washed twice with water, dried on magnesium sulfate and concentrated by evaporation in a vacuum. The residue is chromatographed on silica gel with hexane/0–70% of ether. 188 mg of the title compound is obtained as a colorless oil.

IR: 3700, 3640, 3500, 2940, 2870, 1730, 1610, 1250, 972 cm$^{-1}$.

The initial material for the above-named title compound is produced as follows:

a) 2-pentylbenzyl alcohol 245 ml of a 1.6 molar butyllithium solution in hexane is instilled in a solution of 20.0 g of 2-methylbenzyl alcohol in 185 ml of ether under argon, so that the temperature does not exceed 10° C. Then, it is refluxed for 5 hours, allowed to cool off to 24° C., 22.4 g of 1-bromobutane is instilled and it is stirred for 16 hours at 24° C. The reaction mixture is added to 100 ml of water and extracted three times with 100 ml of ether each. The organic phase is washed with brine, dried on sodium sulfate and concentrated by evaporation in a vacuum. The residue is chromatographed on silica gel with hexane/0–30% of ethyl acetate. 20.1 g o the title compound is obtained as a colorless oil.

IR: 3540, 3320, 2930, 2860, 1605, 750 cm$^{-1}$.

b) 2-pentylbenzyl bromide 3.2 ml of pyridine is added to a solution of 21 g of the above-produced alcohol in 23.8 ml of ether and instilled at −10° C. under argon in 5.1 ml of phosphorus tribromide. It is refluxed for 3 hours and after cooling off to 24° C., the reaction mixture is carefully added to 40 ml of water. It is extracted three times with 150 ml of ether each, the organic phase is washed with brine, dried on sodium sulfate and concentrated by evaporation in a vacuum. The residue is chromatographed on silica gel with hexane/0–6% of ether. 19.5 g of the title compound is obtained as a colorless oil.

IR: 2958, 2930, 2860, 1608, 760 cm$^{-1}$.

c) (5RS)-5-Acetoxy-1-[cis-(2RS)-2-tert-butyldimethylsilyloxymethyl)-(1RS)-cyclohex-1-yl]-6-(2-pentylphenyl)-1,3-hexadiene Analogously to example 1c, 4.1 g of the title compound is obtained as a colorless oil from 5.7 g of the aldehyde produced according to example 12b.

IR: 2930, 2858, 1735, 1605, 1240, 990, 845, 750 cm$^{-1}$.

d) cis-(1RS)-1-Formyl-(2RS)-[(1E,3E)-(5RS)-5-acetoxy-6-(2-pentylphenyl)-1,3-hexadienyl)-cyclohexane diastereomer A and diastereomer B 4.68 g of tetrabutylammonium fluoride is added to a solution of 3.8 g of the above-produced acetate in 90 ml of tetrahydrofuran at 0° C. under argon and stirred first for 30 minutes at 0° C., then for 4.5 hours at 24° C. It is diluted with ether, the organic phase is washed twice with brine/water (1+1), dried on sodium sulfate and concentrated by evaporation in a vacuum. The residue is chromatographed on silica gel with hexane/0–30% of ethyl acetate. In this way, first 690 mg of the nonpolar diastereomer and then 1.05 g of the polar diastereomer cis-(1RS)-1-hydroxymethyl-(2RS)-[(1E,3E)-(5RS)-5-acetoxy-6-(2-pentylphenyl)-1,3-hexadienyl)-cyclohexane are obtained as colorless oils.

IR (nonpolar diastereomer): 3440, 2925, 2857, 1738, 1605, 1235, 990, 750 cm$^{-1}$.

IR (polar diastereomer): 3450, 2925, 2855, 1738, 1605, 1235, 990, 750 cm$^{-1}$.

685 mg of the above-produced alcohol (nonpolar diastereomer) dissolved in 17 ml of methylene chloride is mixed at 0° C. under argon with 3.5 g of Collins reagent and stirred for 20 minutes at 0° C. It is diluted with hexane/ether (2+1), filtered off on Celite, subsequently washed with hexane/ether (2+1) and concentrated by evaporation in a vacuum. The aldehyde thus obtained (diastereomer A) is used without further purification.

Analogously to the above-described method, the aldehyde (diastereomer B) is obtained from 1.05 g of the above-produced alcohol (polar diastereomer).

EXAMPLE 65

(±)-(5RS)-5-Acetoxy-5-[cis-(2RS)-2-((1E,3E)-(5RS)-5-acetoxy-6-(2-pentylphenyl)-1,3-hexadienyl)-(1RS)-cyclohex-1-yl]-pentan-1-ol (diastereomer B)

Analogously to example 64, 252 mg of the title compound is obtained as a colorless oil from 980 mg of the aldehyde (diastereomer B) produced according to example 64d.

IR: 3700, 3620, 3480, 2938, 2870, 1732, 1605, 1250, 992 cm$^{-1}$.

EXAMPLE 66

(±)-(5RS)-5-Acetoxy-5-[cis-(2RS)-2-((1E,3E)-(5RS)-5-acetoxy-6-(2-pentylphenyl)-1,3-hexadienyl)-(1RS)-cyclohex-1-yl]-pentanoic Acid Diastereomer A1 and A2 diastereomer 185 mg of the alcohol, produced according to example 64, in 20 ml of methylene chloride is mixed at 0° C. under argon with 1.1 g of Collins reagent (chromic acid-pyridine complex) and stirred for 30 minutes at 0° C. It is diluted with hexane/ether (1+1), filtered off on Celite, subsequently washed with hexane/ether (1+1) and concentrated by evaporation in a vacuum. The residue is dissolved in 15 ml of acetone, 0.35 ml of Jones reagent (J. Chem. Soc. 1953, 2555) is instilled at −30° C. with stirring and stirred for 20 minutes at −20° C. Then, 0.5 ml of isopropanol is added, stirred for 10 minutes at −20° C., diluted with ether, washed neutral with brine/water (1+1), dried on sodium sulfate and concentrated by evaporation in a vacuum. The residue is chromatographed on silica gel with hexane/0–60% of ethyl acetate. First 75 mg of nonpolar diastereomer (diastereomer A1) and then 50 mg of polar diastereomer (diastereomer A2) are obtained as colorless oils.

IR (diastereomer A1): 3520, 3180, 2937, 2860, 1730, 1605, 1250, 990 $cm^{-1}$.

IR (diastereomer A2): 3520, 3100, 2937, 2860, 1730, 1605, 1248, 992 $cm^{-1}$.

EXAMPLE 67

(±)-(5RS)-5-Acetoxy-5-[cis-(2RS)-2-((1E,3E)-(5RS)-5-acetoxy-6-(2-pentylphenyl)-1,3-hexadienyl)-(1RS)-cyclohex-1-yl]-pentanoic Acid Diastereomer B1 and diastereomer B2

Analogously to example 66, 95 mg of nonpolar diastereomer (diastereomer B1) and 60 mg of polar diastereomer (diastereomer B2) of the title compound are obtained as colorless oils from 240 mg of the alcohol produced according to example 65.

IR (diastereomer B1): 3520, 3150, 2935, 2860, 1730, 1605, 1250, 992 $cm^{-1}$.

IR (diastereomer B2): 3520, 3100, 2937, 2862, 1730, 1605, 1248, 992 $cm^{-1}$.

EXAMPLE 68

(±)-(5RS)-5-Acetoxy-5-[cis-(2RS)-2-((1E,3E)-(5RS)-5-hydroxy-6-(2-pentylphenyl)-1,3-hexadienyl)-(1RS)-cyclohex-1-yl]-pentanoic Acid Diastereomer A1

Analogously to example 4, 35.4 mg of the title compound is obtained as a colorless oil from 70 mg of the diacetate (diastereomer A1) produced according to example 66.

IR: 3680, 3600, 3410, 2930, 2860, 1725, 1605, 1255, 992 $cm^{-1}$.

EXAMPLE 69

(±)-(5RS)-5-Acetoxy-5-[cis-(2RS)-2-((1E,3E)-(5RS)-5-hydroxy-6-(2-pentylphenyl)-1,3-hexadienyl)-(1RS)-cyclohex-1-yl]-pentanoic Acid Diastereomer B1

Analogously to example 4, 55 mg of the title compound is obtained as a colorless oil from 90 mg of the diacetate (diastereomer B1) produced according to example 67.

IR: 3690, 3600, 3400 2930, 2860, 1725, 1603, 1255, 993 $cm^{-1}$.

EXAMPLE 70

(±)-(5RS)-5-Acetoxy-5-[cis-(2RS)-2-((1E,3E)-(5RS)-5-hydroxy-6-(2-pentylphenyl)-1,3-hexadienyl)-(1RS)-cyclohex-1-yl]-pentanoic Acid Diastereomer A2

Analogously to example 4, 16.4 mg of the title compound is obtained as a colorless oil from 45 mg of the diacetate (diastereomer A2) produced according to example 66.

IR: 3600, 3520, 3420, 2930, 2860, 1730, 1605, 1250, 992 $cm^{-1}$.

EXAMPLE 71

(±)-(5RS)-5-Acetoxy-5-[cis-(2RS)-2-((1E,3E)-(5RS)-5-hydroxy-6-(2-pentylphenyl)-1,3-hexadienyl)-(1RS)-cyclohex-1-yl]-pentanoic Acid Diastereomer B2

Analogously to example 4, 22.4 mg of the title compound is obtained as a colorless oil from 55 mg of the diacetate (diastereomer B2) produced according to example 67.

IR: 3600, 3520, 3400, 2935, 2860, 1730, 1605, 1255, 992 $cm^{-1}$.

EXAMPLE 72

(±)-(5RS)-5-Hydroxy-5-[cis-(2RS)-2-((1E,3E)-(5RS)-5-hydroxy-6-(2-pentylphenyl)-1,3-hexadienyl)-(1RS)-cyclohex-1-yl]-pentanoic Acid Diastereomer A1

Analogously to example 62, 14.8 mg of the title compound is obtained as a colorless oil from 28 mg of the monoacetate produced according to example 68.

IR: 3680, 3520, 2930, 2860, 1728, 1605, 1248, 992 $cm^{-1}$.

EXAMPLE 73

(±)-(5RS)-5-Hydroxy-5-[cis-(2RS)-2-((1E,3E)-(5RS)-5-hydroxy-6-(2-pentylphenyl)-1,3-hexadienyl)-(1RS)-cyclohex-1-yl]-pentanoic Acid Diastereomer B1

Analogously to example 62, 15.2 mg of the title compound is obtained as a colorless oil from 38 mg of the monoacetate produced according to example 69.

IR: 3680, 3510, 2935, 2860, 1725, 1605, 1250, 992 $cm^{-1}$.

EXAMPLE 74

(±)-(5RS)-5-Hydroxy-5-[cis-(2RS)-2-((1E,3E)-(5RS)-5-hydroxy-6-(2-pentylphenyl)-1,3-hexadienyl)-(1RS)-cyclohex-1-yl]-pentanoic Acid Diastereomer A2

Analogously to example 62, 3.8 mg of the title compound is obtained as a colorless oil from 13 mg of the monoacetate produced according to example 70.

IR: 3690, 3610, 3440, 2935, 2862, 1722, 1605, 1260, 993 $cm^{-1}$.

EXAMPLE 75

(±)-(5RS)-5-Hydroxy-5-[cis-(2RS)-2-((1E,3E)-(5RS)-5-hydroxy-6-(2-pentylphenyl)-1,3-hexadienyl)-(1RS)-cyclohex-1-yl]-pentanoic Acid Diastereomer B2

Analogously to example 62, 7.4 mg of the title compound is obtained as a colorless oil from 18 mg of the monoacetate produced according to example 71.

IR: 3680, 3520, 3410, 2930, 2860, 1720, 1605, 1245, 992 $cm^{-1}$.

We claim:

1. A compound of formula I,

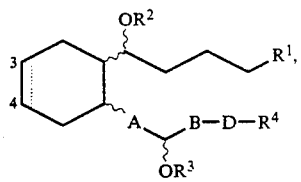 (I)

wherein the radicals have the following meanings:

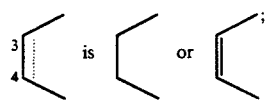

$R^1$ is $CH_2OH$; $CH_3$; $CF_3$; $COOR^5$, wherein
  $R^5$ is H, a $C_{1-10}$-alkyl radical, a $C_{3-10}$-cycloalkyl radical, a $C_{6-10}$-aryl radical optionally substituted by 1-3 chlorine, bromine, phenyl, $C_{1-4}$-alkyl, $C_{1-4}$-alkoxy, chloromethyl, fluoromethyl, trifluoromethyl, carboxy or hydroxy groups, a —$CH_2$—CO—$C_{6-10}$-aryl radical; or a 5-6-member aromatic heterocyclic radical having at least 1 heteroatom N, S or O, or
$R^1$ is $CONHR^6$ wherein
  $R^6$ is a $C_{1-10}$-alkanoyl or -alkanesulfonyl radical or an $R^5$ radical;
A is a trans, trans—CH=CH—CH=CH— group or a tetramethylene group;
B is a straight-chain or branched-chain, saturated or unsaturated $C_{1-10}$-alkylene group, optionally substituted by fluorine, or the group

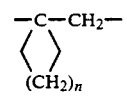

wherein n is 1, 2 or 3; and
D is a direction bond, oxygen, sulfur, a —C≡C group or a —CH=$CR^7$ group wherein
  $R^7$ is H, $C_{1-5}$-alkyl, chlorine, bromine or

or
B and D together are a direct bond;
$R^2$ and $R^3$ are the same or different and are H or a $C_{1-15}$-organic carboxylic or sulfonic acid radical;
$R^1$ and $R^2$ together are a carbonyl group;
$R^4$ is H; $C_{1-10}$-alkyl optionally substituted by chlorine or bromine; $C_{3-10}$-cycloalkyl; a $C_{6-1}$-aryl radical optionally substituted by 1-3 chlorine, bromine, phenyl $C_{1-4}$ alkyl $C_{1-4}$ alkoxy, chloromethyl, fluoromethyl, trifluoromethyl, carboxy or hydroxy groups; or a 5-6-member aromatic heterocyclic radical having at least 1 heteroatom N, S or O; and
when $R^5$ is H, a salt thereof with a physiologically compatible base or a cyclodextrin clathrate thereof.

2. A compound of claim 1, wherein:

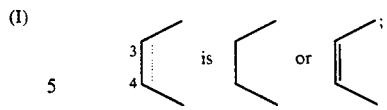

$R^1$ is $CH_2OH$, $COOR^5$ wherein $R^5$ I H, a $C_{1-10}$-alkyl radical, a $C_{5-6}$-cycloalkyl radical, a phenyl radical optionally substituted by 1-2 chlorine, bromine, phenyl, $C_{1-4}$ alkyl, $C_{1-4}$ alkoxy, chloromethyl, fluoromethyl, trifluoromethyl, carboxy or hydroxy groups, or
$R^1$ is $CONHR^6$ wherein
  $R^6$ is a $C_{1-10}$-alkanoyl or -alkanesulfonyl radical or an $R^5$ radical;
A is a trans, trans—CH=CH—CH=CH— group or a tetramethylene group;
B is a straight-chain or branched-chain, saturated or unsaturated $C_{1-10}$-alkylene group optionally substituted by fluorine, or the group

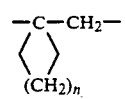

wherein n is 1, 2 or 3; and
D is a direct bond, oxygen, sulfur, a —C≡C group or a —CH=$CR^7$ group wherein
  $R^7$ is H, $C_{1-5}$-alkyl, chlorine, bromine or

or
B and D together are a direct bond;
$R^2$ and $R^3$ are the same or different and are H or a $C_{1-15}$-organic carboxylic or sulfonic acid radical;
$R^1$ and $R^2$ together are a carbonyl group;
$R^4$ is a H, $C_{1-10}$-alkyl, $C_{5-6}$-cycloalkyl, a phenyl radical optionally substituted by 1-2 chlorine, bromine, phenyl, $C_{1-4}$-alkyl, $C_{1-4}$-alkoxy, chloromethyl, fluoromethyl, trifluoromethyl, carboxy, or hydroxy groups, and
wherein $R^5$ is H, a salt thereof with a physiologically compatible base or a cyclodextrin clathrate thereof.

3. A compound of claim 1, wherein:

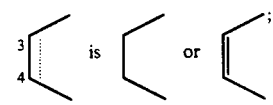

$R^1$ is $CH_2OH$, $COOR^5$ wherein $R^5$ is H, or a $C_{1-4}$-alkyl radical;
A is a trans, trans—CH=CH—CH=CH— group or a tetramethylene group;
B is a straight-chain or branched-chain $C_{1-5}$-alkylene group; and
D is a direct bond or a —C≡C group or a —CH=$CR^7$ group wherein $R^2$ is H or $C_{1-5}$-alkyl;
or

or

B and D together are a direct bond;
R² and R³ are the same or different and are H or a C$_{1-6}$-organic carboxylic or sulfonic acid radical;
R¹ and R² together are a carbonyl group;
R⁴ is H or a C$_{1-10}$-alkyl, and
when R⁵ is H, a salt thereof with a physiologically compatible base or a cyclodextrin clathrate thereof.

4. A compound of claim 1, selected from the group:
(+)-(5RS)5-acetoxy-5-[cis-(6RS)-6-((1E,3E)-(5RS)-5-acetoxy-1,3,tridecadienyl)-(1RS)-3-cyclohexen-1yl]-pentanol nonpolar and polar diastereomers;
(+)-(5RS)5-acetoxy-5-[cis-(6RS)-6-((1E,3E)-(5RS)-5-acetoxy-1,3-tridecadienyl)-(1RS)-3-cyclohexen-1yl]-pentanoic acid diastereomer A;
(+)-(RS)-5-hydroxy-5-[cis-(6RS)-6-((1E,3E)-(5RS)-5-hydroxy-1,3-tridecadienyl)-(1RS)-3-cyclohexen-1-yl]-pentanoic acid diastereomer A;
(+)-(5RS)-5-acetoxy-5-[cis-(6RS)-6-((1E,3E)-(5RS)-5-hydroxy-1,3-tridecadienyl)-(1RS)-3-cyclohexen-1-yl]-pentanoic acid diastereomer A;
(+)-(5RS)-5-hydroxy-5-[cis-(6RS)-6-((1E,3E)-(5RS)-5-hydroxy-1,3-tridecadienyl)-(1RS)-3-cyclohexen-1-yl]-pentanol diastereomer A;
(+)-(5RS)-5-acetoxy-5-[cis-(6RS)-6-((1E,3E)-(5RS)-5-hydroxy-1,3-tridecadienyl)-(1RS)-3-cyclohexen-1-yl]-pentanol diastereomer A;
(+)-(5RS)-5-acetoxy-5-[cis-(4RS)-6-((1E,3E)-(5RS)-5-acetoxy-1,3-tridecadienyl)-(1RS)3-cyclohexen-1-yl]-pentanoic acid diastereomer B;
(+)-(5RS)-5-hydroxy-5-[cis-(6RS)-6-((1E,3E)-(5RS)-5-hydroxy-1,3-tridecadienyl)-(1RS)-3-cyclohexen-1-yl]-pentanoic acid diastereomer B;
(+)-(5RS)-5-acetoxy-5-[cis-(6RS)-6-((1E,3E)-(5RS)-5-hydroxy-1,3-tridecadienyl)-(1RS)-3-cyclohexen-1-yl]-pentanoic acid; diastereomer B;
(+)-(5RS)-5-hydroxy-5-[cis-(6RS)-6-((1E,3E)-(5RS)-5-hydroxy-1,3-tridecadienyl)-(1RS)-3-cyclohexen-1yl]-pentanol diastereomer B;
(+)-(5RS)-5-acetoxy-5-[cis-(6RS)-6-((1E,3E)-(5RS)-5-hydroxy-1,3-tridecadienyl)-(1RS)-3-cyclohexen-1yl]-pentanol diastereomer B;
(+)-(5RS)-5-acetoxy-5-[cis-(2RS)-2-((1E,3E)-(5RS)-5-acetoxy-1,3tridecadienyl)-(1RS)cyclohex-1-yl]-pentanol nonpolar and polar diastereomers;
(+)-(5RS)-5-acetoxy-508 cis-(2RS)-2-((1E,3E)-(5RS)5-acetoxy-1,3-tridecadienyl)-(1RS)-cyclohex-1-yl]-pentanoic acid diastereomer A;
(+)-(5RS)-5-hydroxy-5-[cis-(2RS)-2-((1E,3E)-(5RS)-5-hydroxy-1,3-tridecadienyl)-(1RS)-cyclohex-1-yl]-pentanoic acid diastereomer A;
(+)-(5RS)-5-acetoxy-5-[cis-(2RS)-2-((1E,3E)-(5RS)-5-hydroxy-1,3-tridecadienyl)-(1RS-cyclohex-1-yl]-pentanoic acid diastereomer A;
(+)-(5RS()-5-acetoxy-5-[cis-(2RS)-2-((1E,3E)-(5RS)-5-acetoxy-1,3-tridecadienyl)-(1RS)-cyclohex-1-yl]-pentanoic acid diastereomer B;
(+)-(5RS()-5-hydroxy-5-[cis-(2RS)-2-((1E,3E)-(5RS)-5-hydroxy-1,3-tridecadienyl)-(1RS)-cyclohex-1-yl]-pentanoic acid diastereomer B;
(+)-(5RS()-5-acetoxy-5-[cis-(2RS)-2-((1E,3E)-(5RS)-5-hydroxy-1,3-tridecadienyl)-(1RS)-cyclohex-1-yl]-pentanoic acid diastereomer B;
(+)-(5RS()-5-acetoxy-5-[cis-(6RS)-6-((1E,3E)-(5RS)-5-acetoxy-1,3-tridecadienyl)-(1RS)-cyclohexen-1-yl]-pentanoic acid methyl ester diastereomer A;
(+)-(5RS)-5-hydroxy-5-[cis-(6RS)-6-((1E,3E)-(5RS)-5hydroxy-1,3-tridecadienyl)-(1RS)-3-cyclohexen-1yl]-pentanoic acid methyl ester diastereomer A;
(+)-(5RS)-5-acetoxy-5-[cis-(6RS)-6-((1E,3E)-(5RS)-5hydroxy-1,3-tridecadienyl)-(1RS)-3-cyclohexen-1yl]-pentanoic acid methyl ester diastereomer A;
(+)-(5RS)-5-acetoxy-5-[cis-(2RS)-2-0((1E,3E)-(5RS)-5-acetoxy-1,3-tridecadienyl)-(1RS)-cyclohex-1-yl]-pentanoic acid methyl ester diastereomer A;
(+)-()5RS)-5-hydroxy-5-[cis-(2RS)-2-((1E, 3E-(5RS)-5-hydroxy-1,3-tridecadienyl)-(1RS)-cyclohex-1-yl]-pentanoic acid methyl ester diastereomer A;
(+)-(5RS)-5-acetoxy-5-[cis-(2RS)-2-((1E,3E)-(5RS)-5-hydroxy-1,3-tridecadienyl)-(1RS)-cyclohex-1-yl]-pentanoic acid methyl ester diastereomer A;
(+)-(5RS)-5-hydroxy-5-[cis-(6RS)-6-((1E,3E)-(5RS)-5-hydroxy-1,3-tridecadienyl)-(1RS)-3cyclohex-1-yl]-pentanoic acid-1,5-lactone diastereomer A;
(+)-(5RS)-5-hydroxy-5-[cis-(6RS)-6-((1E,3E)-(5RS)-5-hydroxy-1,3-tridecadienyl)-(1RS)-3cyclohex-1-yl]-pentanoic acid-1,5-lactone diastereomer B;
(+)-(5RS)-5-hydroxy-5-[cis-(2RS)-2-((1E,3E)-(5RS)-5-hydroxy-1,3-tridecadienyl)-(1RS)-cyclohex-1-yl]-pentanoic acid-1,5-lactone diastereomer A;
(+)-(5RS)-5-hydroxy-5-[cis-(2RS)-2-((1E,3E)-(5RS)-5-hydroxy-1,3-tridecadienyl)-(1RS)-cyclohex-1-yl]-pentanoic acid-1,5-lactone diastereomer B;
(+)-(5RS)-5-hydroxy-5-[cis-(6RS)-6-((1E,3E)-(5RS)-5-hydroxy-1,3-tridecadienyl)-(1RS)-3-cyclohexen-1-yl]-pentanoic acid-tris-(hydroxymethyl)-aminomethane salt;
(+)-(5RS)-5-acetoxy-5-[trans(6RS)-6-((1E,3E)-(5RS)-5-acetoxy-1,3-tridecadienyl)-(1RS)-3-cyclohexen-1-yl]-pentanol nonpolar and polar diastereomers;
(+)-(5RS)-5-acetoxy-5-[trans-(6RS)-6-((1E,3E)-(5RS)-5-acetoxy-1,3-tridecadienyl)-(1RS)-cyclohexen-1-yl]-pentanoic acid diastereomer A;
(+)-(RS)-5-hydroxy-5-[trans-(6RS)-6-((1E,3E)-(5RS)-5-hydroxy-1,3-tridecadienyl)-(1RS)-3-cyclohexen-1-yl]-pentanoic acid diastereomer A;
(+)-(5RS)-5-acetoxy-5-[trans-(6RS)-6-((1E,3E)-(5RS)-5-hydroxy-1,3-tridecadienyl)-(1RS)-3-cyclohexen-1-yl]-pentanoic acid diastereomer A;
(+)-(5RS)-5-hydroxy-5-[trans-(6RS)-6-((1E,3E)-(5RS)-5-hydroxy-1,3tridecadienyl)-(1RS)-3-cyclohexen-1-yl]-pentanol diastereomer A;
(+)-(5RS)-5-acetoxy-5-[trans-(6RS)-60((1E,3E)-(5RS)-50-hydroxy-1,3-tridecadienyl)-(1RS)-3-cyclohexen-1-yl]-pentanol; diastereomer A;
(+)-(5RS)-5-acetoxy-5-[trans-(6RS)-6-((1E,3E)-(5RS)-5-acetoxy-1,3-tridecadienyl)-(1RS)-3-cyclohexen-1-yl]-pentanoic acid diastereomer B;
(+)-(5RS)-5-hydroxy-5-[trans-(6RS)-6-((1E,3E)-(5RS)-5-hydroxy-1,3-tridecadienyl)-(1RS)-3-cyclohexen-1-yl]-pentanoic acid diastereomer B;
(+)-(5RS)-5-acetoxy-5-[trans-(6RS)-6-((1E,3E)-(5RS)-5-hydroxy-1,3-tridecadienyl)-(1RS)-3-cyclohexen-1-yl]-pentanoic acid diastereomer B;
(+)-(5RS)-5-hydroxy-5-[trans-(6RS)-6-((1E,3E)-(5RS)-5-hydroxy-1,3-tridecadienyl)-(1RS)-3-cyclohexen-1-yl]-pentanol diastereomer B;

(+)-(5RS)-5-acetoxy-5-[trans-(6RS)-6-((1E,3E)-(5RS)-5-hydroxy-1,3-tridecadienyl)-(1RS)-3-cyclohexen-1-yl]-pentanol diastereomer B;

(+)-(5RS)-5-acetoxy-5-[trans-(2RS)-2-((1E,3E)-(5RS)-5-acetoxy-1,3-tridecadienyl)-(1RS)-cyclohex-1-yl]-pentanol nonpolar and polar diastereomer;

(+)-(5RS)-5-acetoxy-5-[trans-(2RS)-2-((1E,3E)-(5RS)-5-acetoxy-1,3-tridecadienyl)-(1RS)-cyclohex-1-yl]-pentanoic acid diastereomer A;

(+)-(5RS)-5-hydroxy-5-[trans-(2RS)-2-((1E,3E)-(5RS)-5-hydroxy-1,3-tridecadienyl)-(1RS)-cyclohex-1-yl]-pentanoic aid diastereomer A;

(+)-(5RS)-5-acetoxy-5-[trans-(2RS)-2-((1E,1E)-(5RS)-5-hydroxy-1,3-tridecadienyl)-(1RS)-cyclohex-1-yl]-pentanoic acid diastereomer A;

(+)-(5RS)-5-acetoxy-5-[trans-(2RS)-2-((1E,3E)-(5RS)-5-acetoxy-1,3-tridecadienyl)-(1RS)-cyclohex-1-yl]-pentanoic acid diastereomer B;

(+)-(5RS)-5-hydroxy-5-[trans-(2RS)-2-((1E,3E)-(5RS)-5-hydroxy-1,3-tridecadienyl)-(1RS)-cyclohex-1-yl]-pentanoic acid diastereomer B;

(+)-(5RS)-5-acetoxy-5-[trans-(2RS)-2-((1E,3E)-(5RS)-5-hydroxy-1,3-tridecadienyl)-(1RS)-cyclohex-1-yl]-pentanoic acid diastereomer B;

(+)-(5RS)-5-acetoxy-5-[trans-(6RS)-6-((1E,3E)-(5RS)-5-acetoxy-1,3-tridecadienyl)-(1RS)-3-cyclohexen-1-yl]-pentanoic acid methyl ester diastereomer A;

(+)-(5RS)-5-hydroxy-5-[trans-(6RS)-6-((1E,3E)-(5RS)-5-hydroxy-1,3-tridecadienyl)-(1RS)-3-cyclohexen-1-yl]-pentanoic acid methyl ester diastereomer A;

(+)-(5RS)-5-acetoxy-5-[trans-(6RS)-6-((1E,3E)-(5RS)-5-hydroxy-1,3-tridecadienyl)-(1RS)-3-cyclohexen-1-yl]-pentanoic acid methyl ester diastereomer A;

(+)-(5RS)-5-acetoxy-5-[trans-(2RS)-2-((1E,3E)-(5RS)-5-acetoxy-1,3-tridecadienyl)-(1RS)-3-cyclohex-1-yl]-pentanoic acid methyl ester diastereomer A;

(+)-(5RS)-5-hydroxy-5-[trans-(2RS)-2-((1E,3E)-(5RS)-5-hydroxy-1,3-tridecadienyl)-(1RS)-cyclohex-1-yl]-pentanoic acid methyl ester diastereomer A;

(+)-(5RS)-5-acetoxy-5-[trans-(2RS)-2-((1E,3E)-(5RS)-5-hydroxy-1,3-tridecadienyl)-(1RS)-cyclohex-1-yl]-pentanoic acid methyl ester diastereomer A;

(+)-(5RS)-5-hydroxy-5-[trans-(6RS)-6-((1E,3E)-(5RS)-5-hydroxy-1,3-tridecadienyl)-(1RS)-3-cyclohexen-1-yl]-pentanoic acid-1,5-lactone diastereomer A;

(+)-(5RS)-5-hydroxy-5-[trans-(6RS)-6-((1E,3E)-(5RS)-5-hydroxy-1,3-tridecadienyl)-(1RS)-3-cyclohexen-1-yl]-pentanoic acid-1,5-lactone diastereomer B;

(+)-(5RS)-5-hydroxy-5-[trans-(2RS)-2-((1E,3E)-(5RS)-5-hydroxy-1,3-tridecadienyl)-(1RS)-cyclohex-1-yl]-pentanoic acid-1,5-lactone diastereomer A;

(+)-(5RS)-5-hydroxy-5-[trans-(2RS)-2-((1E,3E)-(5RS)-5-hydroxy-1,3-tridecadienyl)-(1RS)-cyclohex-1-yl]-pentanoic acid-1,5-lactone diastereomer B;

(+)-(5RS)-5-hydroxy-5-[trans-(6RS)-6-((1E,3E)-(5RS)-5-hydroxy-1,3-tridecadienyl)-(1RS)-3-cyclohexen-1-yl]-pentanoic acid-tris-hydroxymethyl)-aminomethane salt;

(+)-(5RS)-5-acetoxy-5-[cis-(2RS)-2-((1E,3E)-(5RS)-5-hydroxy-trideca-1,3-dien-7-inyl)-(1RS)-cyclohex-1yl]-pentanoic acid nonpolar and polar diastereomer;

(+)-(5RS)-5-acetoxy-5-[cis-(2RS)-2-((1E,3E,7Z)-(5RS)-5-hydroxy-1,3,7-tridecatrienyl)-(1RS)-cyclohex-1-yl]-pentanoic acid diastereomers A and B;

(+)-(5RS)-5-hydroxy-5-[cis-(2RS)-2-((1E,3E,7Z)-(5RS)-5-hydroxy-1,3,7-tridecatrienyl)-(1RS)-cyclohex-1-yl]-pentanoic acid diastereomer A;

(+)-(5RS)-5-hydroxy-5-[cis-(2RS)-5-((1E,3E,7Z)-(5RS)-5-hydroxy-1,3,7-tridecatrienyl)-(1RS)-cyclohex-1-yl]-pentanoic acid (diastereomer B);

(+)-(5RS)-5-acetoxy-5-[cis-(2RS)-2-((1E,3E)-(5RS)-5-acetoxy-6-(2-pentylphenyl)-1,3-hexadienyl)-(1RS)-cyclohex-1-yl]-pentan-1-ol diastereomer A;

(+)-(5RS)-5-acetoxy-5-[cis-(2RS)-2-((1E,3E)-(5RS)-5-acetoxy-6-(2-pentylphenyl)-1,3-hexadienyl)-(1RS)-cyclohex-1-yl]-pentan-1-ol (diastereomer B);

(+)-(5RS)-5-acetoxy-5-[cis-(2RS)-2-((1E,3E)-(5RS)-5-acetoxy-6-(2-pentylphenyl)-1,3-hexadienyl)-(1RS)-cyclohex-1-yl]-pentanoic acid diastereomer A1 and A2 diastereomer;

(+)-(5RS)-5-acetoxy-5-[cis-(2RS)-2-((1E,3E)-(5RS)-5-acetoxy-6-(2-pentylphenyl)-1,3-hexadienyl)-(1RS)-cyclohex-1-yl]-pentanoic acid diastereomer B1 and diastereomer B2;

(+)-(5RS)-5-acetoxy-5-[cis-(2RS)-2-((1E,3E)-(5RS)-5-hydroxy-6-(2-pentylphenyl)-1,3-hexadienyl)-(1RS)-cyclohex-1-yl]-pentanoic acid diastereomer A1;

(+)-(5RS)-5-acetoxy-5-[cis-(2RS)-2-((1E,3E)-(5RS)-5-hydroxy-6-(2-pentylphenyl)-1,3-hexadienyl)-(1RS)-cyclohex-1-yl]-pentanoic acid diastereomer B1;

(+)-(5RS)-5-acetoxy-5-[cis-(2RS)-2-((1E,3E)-(5RS)-5-hydroxy-6-(2-pentylphenyl)-1,3-hexadienyl)-(1RS)-cyclohex-1-yl]-pentanoic acid diastereomer A2;

(+)-(5RS)-5-acetoxy-5-[cis-(2RS)-2-((1E,3E)-(5RS)-5-hydroxy-6-(2-pentylphenyl)-1,3-hexadienyl)-(1RS)-cyclohex-1-yl]-pentanoic acid diastereomer B2;

(+)-(5RS)-5-hydroxy-5-[cis-(2RS)-2-((1E,3E)-(5RS)-5-hydroxy-6-(2-pentylphenyl)-1,3-hexadienyl)-(1RS)-cyclohex-1-yl]-pentanoic acid diastereomer A1;

(+)-(5RS)-5-hydroxy-5-[cis-(2RS)-2-((1E,3E)-(5RS)-5-hydroxy-6-(2-pentylphenyl)-1,3-hexadienyl)-(1RS)-cyclohex-1-yl]-pentanoic acid diastereomer B1;

(+)-(5RS)-5-hydroxy-5-[cis-(2RS)-2-((1E,3E)-(5RS)-5-hydroxy-6-(2-pentylphenyl)-1,3-hexadienyl)-(1RS)-cyclohex-1-yl]-pentanoic acid diastereomer A2; or (+)-(5RS)-5-hydroxy-5-[cis-(2RS)-2-((1E,3E)-(5RS)5-hydroxy-6-(2-pentylphenyl)-1,3-hexadienyl)-(1RS)-cyclohex-1-yl]-pentanoic acid diastereomer B2.

5. A pharmaceutical preparation, comprising an effective amount of a compound of claim 1 and a pharmaceutically acceptable excipient.

6. A pharmaceutical preparation of claim 5, in a form suitable for topical administration.

7. A pharmaceutical preparation of claim 6, in the form of a solution, lotion, ointment, cream or plaster.

8. A pharmaceutical preparation of claim 6, in the form of a lotion or ointment, wherein the active ingredient is present at a concentration of 0.0001% to 1%.

9. A pharmaceutical preparation of claim 5, in a form suitable for inhalation therapy.

10. A pharmaceutical preparation of claim 5, in a form suitable for oral administration.

11. A pharmaceutical preparation of claim 5, in a form suitable for rectal administration.

12. A pharmaceutical preparation of claim 5, further comprising a lipoxygenase inhibitor, a cyclooxygenase inhibitor, a prostacyclin agonist, a thromboxane antagonist, a leukotriene-$D_4$ antagonist, a leukotriene-$E_4$ antagonist, a leukotriene-$F_4$ antagonist, a phosphodiesterase inhibitor, a calcium antagonist or a PAF antagonist.

13. A method of treating an inflammatory or allergic disease, comprising administering to a patient an effective amount of a compound of claim 1.

14. A method of treating an inflammatory or allergic skin disease, comprising administering to a patient an effective amount of a compound of claim 1.

15. A method of claim 13, wherein the disease is arthritis, asthma, rhinitis or inflammatory intestinal disease.

16. A method of claim 14, wherein the disease is eczema, erythema, psoriasis, atopic dermatitis, pruritus or acne.

17. A method of treating fungal disease of the skin, comprising administering to a patient an effective amount of a compound of claim 1.

18. A process for the production of a compound of formula I of claim 1, comprising
reacting an aldehyde of formula II,

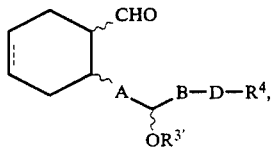
(II)

wherein A, B, D, and $R^4$ have the above-indicated meanings, and $R^{3'}$ is a silyl protecting group, optionally after protection of free hydroxy groups with a magnesium organic compound of formula III, $$X-Mg-CH_2-CH_2-CH_2-CH_2-O-R^8 \quad \text{(III)},$$

wherein

X is chlorine, bromine or iodine and $R^8$ is an easily cleavable ether radical, and optionally separating isomers in any sequence, releasing protected hydroxy groups, and/or esterifying a free hydroxy group and/or oxidizing the 1-hydroxy group to carboxylic acid, and/or hydrogenating double bonds; and/or saponifying or reducing an esterified carboxyl group when $R^1$ is $COOR^5$; and/or esterifying a carboxyl group when $R^5$ is H; and/or converting a free carboxyl group, when $R^5$ is H, to an amide, wherein $R^1$ is $CONHR^6$, or converting a carboxyl group with a physiologically compatible base to a salt.

* * * * *

UNITED STATES PATENT AND TRADEMARK OFFICE
CERTIFICATE OF CORRECTION

PATENT NO. : 5,187,286  
DATED : February 16, 1993  
INVENTOR(S) : Werner SKUBALLA et al.

Page 1 of 2

It is certified that error appears in the above-identified patent and that said Letters Patent is hereby corrected as shown below:

Claim 3, Col. 42, line 67: Change $R^2$ to read -- $R^7$ --
Claim 4, Col. 44, line 1: Change (5RS() to read --(5RS)--
Claim 4, Col. 44, line 4: Change (5RS() to read --(5RS)--
Claim 4, Col. 44, line 8: Change (5hydroxy) to read -- 5-hydroxy --
Claim 4, Col. 44, line 11: Change (5hydroxy) to read -- 5-hydroxy --
Claim 4, Col. 44, line 13: Change 2-O to read -- 2- --
Claim 4, Col. 44, line 16: Change ()5RS) to read -- (5RS) --
Claim 4, Col. 44, line 23: Change (3cyclohex) to read -- 3-cyclohexen --
Claim 4, Col. 44, line 54: Change (6O) to read -- 6- --
Claim 4, Col. 44, line 55: Change (5O) to read -- 5- --
Claim 4, Col. 45, Line 58: After tris- insert (

UNITED STATES PATENT AND TRADEMARK OFFICE
CERTIFICATE OF CORRECTION

PATENT NO. : 5,187,286
DATED : February 16, 1993
INVENTOR(S) : Werner SKUBALLA et al It is certified that error appears in the above-indentified patent and that said Letters Patent is hereby corrected as shown below:

Claim 12, Col. 46, line 64: Insert space after leukotriene-$E_4$.

Signed and Sealed this

Nineteenth Day of July, 1994

Attest:

BRUCE LEHMAN

*Attesting Officer*  *Commissioner of Patents and Trademarks*